US010203274B2

(12) United States Patent
Ruan et al.

(10) Patent No.: US 10,203,274 B2
(45) Date of Patent: Feb. 12, 2019

(54) OPTICAL FOCUSING INSIDE SCATTERING MEDIA WITH TIME-REVERSED ULTRASOUND MICROBUBBLE ENCODED (TRUME) LIGHT

(71) Applicant: California Institute of Technology, Pasadena, CA (US)

(72) Inventors: Haowen Ruan, Pasadena, CA (US); Mooseok Jang, Pasadena, CA (US); Changhuei Yang, South Pasadena, CA (US); Daifa Wang, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/181,160

(22) Filed: Jun. 13, 2016

(65) Prior Publication Data
US 2016/0363527 A1 Dec. 15, 2016

Related U.S. Application Data

(60) Provisional application No. 62/174,858, filed on Jun. 12, 2015.

(51) Int. Cl.
*G01N 15/14* (2006.01)
*A61B 5/00* (2006.01)
(Continued)

(52) U.S. Cl.
CPC ............... *G01N 15/14* (2013.01); *A61B 5/00* (2013.01); *G01N 21/453* (2013.01);
(Continued)

(58) Field of Classification Search
CPC .......... G01N 15/14; G01N 2015/1006; G01N 2015/1486; G01N 2021/473;
(Continued)

(56) References Cited

U.S. PATENT DOCUMENTS 3,947,123 A * 3/1976 Carlson .............. G01N 15/1434
356/338
2002/0108859 A1* 8/2002 Wang ........................ B07C 5/34
204/547

(Continued)

OTHER PUBLICATIONS

Mosk, A. P., Lagendijk, A., Lerosey, G. & Fink, M. Controlling waves in space and time for imaging and focusing in complex media. Nature Photonics 6, 283-292 (2012).

(Continued)

*Primary Examiner* — Tri T Ton
(74) *Attorney, Agent, or Firm* — Gates & Cooper LLP

(57) ABSTRACT

A method for irradiating scattering medium, including modifying a particle's response to electromagnetic radiation irradiating the particle in a scattering medium, wherein the electromagnetic radiation is scattered by the scattering medium, and modulated by the modifying, into scattered electromagnetic radiation comprising a scattered field; forming a phase conjugate field, wherein the phase conjugate field is a phase conjugate of the scattered field; and irradiating the scattering medium with the phase conjugate field, wherein the phase conjugate field forms a focus at a target defined by the particle.

17 Claims, 11 Drawing Sheets

(51) Int. Cl.
*G01N 21/45* (2006.01)
*G01N 21/47* (2006.01)
(52) U.S. Cl.
CPC ..... *G01N 21/4788* (2013.01); *G01N 21/4795* (2013.01); *G01N 2021/473* (2013.01)
(58) Field of Classification Search
CPC .............. G01N 21/1702; G01N 21/453; G01N 21/4788; G01N 21/4795; G01N 21/49; A61B 5/00
USPC .......................................... 356/335–343, 450
See application file for complete search history.

(56) References Cited

U.S. PATENT DOCUMENTS

| | | | | |
|---|---|---|---|---|
| 2006/0144126 | A1* | 7/2006 | O'Brien | G01N 1/2202 73/23.42 |
| 2008/0204749 | A1* | 8/2008 | Haddock | G01N 15/0205 356/335 |
| 2011/0071402 | A1* | 3/2011 | Masumura | G01N 21/4795 600/476 |
| 2012/0070817 | A1* | 3/2012 | Wang | A61B 5/0059 435/3 |

OTHER PUBLICATIONS

Vellekoop, I. M. Feedback-based wavefront shaping. Opt. Express 23, 12189 (2015).
Kim, M., Choi, W., Choi, Y., Yoon, C. & Choi, W. Transmission matrix of a scattering medium and its applications in biophotonics. Opt. Express 23, 12648 (2015).
Yu, H. et al. Recent advances in wavefront shaping techniques for biomedical applications. Curr. Appl. Phys. 15, 632-641 (2015).
Vellekoop, I. M. & Mosk, A. P. Focusing coherent light through opaque strongly scattering media. Opt. Lett. 32, 2309-2311 (2007).
Yaqoob, Z., Psaltis, D., Feld, M. S. & Yang, C. Optical phase conjugation for turbidity suppression in biological samples. Nat Phot. 2, 110-115 (2008).
Cui, M. & Yang, C. Implementation of a digital optical phase conjugation system and its application to study the robustness of turbidity suppression by phase conjugation. Opt. Express 18, 3444-3455 (2010).
Popoff, S. M. et al. Measuring the Transmission Matrix in Optics: An Approach to the Study and Control of Light Propagation in Disordered Media. Phys. Rev. Lett. 104, 100601 (2010).
Yu, H. et al. Measuring Large Optical Transmission Matrices of Disordered Media. Phys. Rev. Lett. 111, 153902 (2013).
Chaigne, T. et al. Controlling light in scattering media non-invasively using the photoacoustic transmission matrix. Nat. Photonics 8, 58-64 (2014).
Hsieh, C., Pu, Y., Grange, R. & Psaltis, D. Digital phase conjugation of second harmonic radiation emitted by nanoparticles in turbid media. Opt. Express 18, 533-537 (2010).
Vellekoop, I. M., Cui, M. & Yang, C. Digital optical phase conjugation of fluorescence in turbid tissue. Appl. Phys. Lett. 101, 081108 (2012).
Katz, O., Small, E., Guan, Y. & Silberberg, Y. Noninvasive nonlinear focusing and imaging through strongly scattering turbid layers. Optica 1, 170 (2014).
Zhou, E. H., Ruan, H., Yang, C. & Judkewitz, B. Focusing on moving targets through scattering samples. Optica 1, 227 (2014).
Ma, C., Xu, X., Liu, Y. & Wang, L. V. Time-reversed adapted-perturbation (TRAP) optical focusing onto dynamic objects inside scattering media. Nat. Photonics 8, 931-936 (2014).
Kong, F. et al. Photoacoustic-guided convergence of light through optically diffusive media. Opt. Lett. 36, 2053-5 (2011).
Caravaca-Aguirre, A. M. et al. High contrast three-dimensional photoacoustic imaging through scattering media by localized optical fluence enhancement. Opt. Express 21, 26671 (2013).

Lai, P. Wang, L. Tay, J. W. & Wang, L. V. Photoacoustically guided wavefront shaping for enhanced optical focusing in scattering media. Nat. Photonics 9, 126-132 (2015).
Xu, X., Liu, H. & Wang, L. V. Time-reversed ultrasonically encoded optical focusing into scattering media. Nat. Photonics 5, 154-157 (2011).
Wang, Y. M., Judkewitz, B., DiMarzio, C. A. & Yang, C. Deep-tissue focal fluorescence imaging with digitally time-reversed ultrasound-encoded light. Nat Commun 3, 928 (2012).
Si, K., Fiolka, R. & Cui, M. Fluorescence imaging beyond the ballistic regime by ultrasound-pulse-guided digital phase conjugation. Nat. Photonics 6, 657-661 (2012).
Jang, M., Ruan, H., Judkewitz, B. & Yang, C. Model for estimating the penetration depth limit of the time-reversed ultrasonically encoded optical focusing technique. Opt Express 22, 5787-5807 (2014).
Kothapalli, S.-R. & Wang, L. V. Ultrasound-modulated optical microscopy. J. Biomed. Opt. 13, 054046, 2008.
Si, K., Fiolka, R. & Cui, M. Breaking the spatial resolution barrier via iterative sound-light interaction in deep tissue microscopy. Sci. Rep. 2, 748 (2012).
Ruan, H., Jang, M., Judkewitz, B. & Yang, C. Iterative time-reversed ultrasonically encoded light focusing in backscattering mode. Sci. Rep. 4, 7156 (2014).
Suzuki, Y., Tay, J. W., Yang, Q. & Wang, L. V. Continuous scanning of a time-reversed ultrasonically encoded optical focus by reflection-mode digital phase conjugation. Opt. Lett. 39, 3441-4 (2014).
Judkewitz, B., Wang, Y., Horstmeyer, R., Mathy, A., & Yang, C., Speckle-scale focusing in the diffusive regime with time reversal of variance-encoded light (TROVE). Nat. Photonics 7, 300-305 (2013).
Lindner, J. R. Microbubbles in medical imaging: current applications and future directions. Nature Reviews 3, 527-532 (2004).
Goertz, D. E. et al. High frequency nonlinear B-scan imaging of microbubble contrast agents. IEEE Trans. Ultrason. Ferroelectr. Freq. Control 52, 65-79 (2005).
Benchimol, M. J. et al. Phospholipid/Carbocyanine Dye-Shelled Microbubbles as Ultrasoung-Modulated Fluorescent Contrast Agents. Soft Matter 9, 2384-2388 (2013).
Liu, Y., Feshitan, J. A., Wei, M.-Y., Borden, M. A. & Yuan, B. Ultrasound-modulated fluorescence based on fluorescent microbubbles. J. Biomed. Opt. 19, 085005 (2014).
Ruan, H. Mather, M. L. & Morgan, S. P. Ultrasound modulated optical tomography contrast enhancement with non-linear oscillation of microbubbles. Quant. Imaging Med. Surg. 5, 9-16 (2015).
Jang, M., Ruan, H., Zhou, H., Judkewitz, B. & Yang, C. Method for auto-alignment of digital optical phase conjugation systems based on digital propogation. Opt. Express 22, 14054-71 (2014).
Yamaguchi, I., Matsumura, T. & Kato, J.-I. Phase-shifting color digital holography. Opt. Lett. 27, 1108-10 (2002).
Vellekoop, I. M. Controlling the propagation of light in disordered scattering media. PhD Thesis, Univ. Twente (2008).
Shekhar, H., Rychak, J. J. & Doyley, M. M. Modifying the size distribution of microbubble contrast agents for high-frequency subharmonic imaging. Med. Phys. 40, 082903-1-082903-10 (2013).
Pancholi, K. P., Farook, U., Moaleji, R., Stride, E. & Edirisinghe, M. J. Novel methods for preparing phospholipid coated microbubbles. Eur. Biophys. J. 37, 515-20 (2008).
Palanchon, P., Klein, J. & de Jong, N. Production of standardized air bubbles: Application to embolism studies. Rev. Sci. Instrum. 74, 2558 (2003).
Jang, M. et al. Relation between speckle decorrelation and optical phase conjugation (OPC)-based turbidity suppression through dynamic scattering media: a study on in vivo mouse skin. Biomed. Opt. Express 6, 72 (2015).
Chomas, J. E., Dayton, P., Allen, J., Morgan, K. & Ferrara, K. W. Mechanisms of contrast agent destruction. IEEE Trans. Ultrason. Ferroelectr. Freq. Control 48, 232-48 (2001).
Ferrara, K., Pollard, R. & Borden, M. Ultrasound microbubble contrast agents: fundamentals and application to gene and drug delivery. Annu. Rev. Biomed. Eng. 9, 415-447 (2007).
Shapiro, M. G. et al. Biogenic gas nanostructures as ultrasonic molecular reporters. Nat. Nanotechnol. 9, 311-316 (2014).

(56) References Cited

OTHER PUBLICATIONS

El-Sayed, I. H., Huang, X. & El-Sayed, M. A. Selective laser photo-thermal therapy of epithelial carcinoma using anti-EGFR antibody conjugated gold nanoparticles. Cancer Lett. 239, 129-135 (2006).

Gradinaru, V., Mogri, M., Thompson, K.R., J. M. & Deisseroth, K. Optical deconstruction of parkinsonian neural circuitry. Science 324, 354-359 (2009).

Shen, D. & McGough, R. J. A 2D fast near-field method for calculating near-field pressures generated by apodized rectangular pistons. J. Acoust. Soc. Am. 124,1526-1537 (2008).

Raum, K. & O'Brien, W. D. Pulse-echo field distribution measurement technique for high-frequency ultrasound sources. IEEE Trans. Ultrason. Ferroelectr. Freq. Control 44, 810-815 (1997).

Haowen Ruan et. al., "Optical focusing inside scattering media with time-reversed ultrasound microbubble encoded light," Haowen Ruan, Mooseok Jang, and Changhuei Yang, Nature communications, 6:8968 | DOI: 10.1038/ncomms9968 §www.nature.com/naturecommunications (Nov. 24, 2015) and Supplementary Information.

website entitled/accessible from "http://holoeye.com/spatial-light-modulators/."

Ruan, H., et al., "Optical focusing inside scattering media with time-reversed ultrasound microbubble encoded light", Nature Communications, Nov. 24, 2015, pp. 1-39. Nature communications, 6:8968 | DOI: 10.1038/ncomms9968.

\* cited by examiner

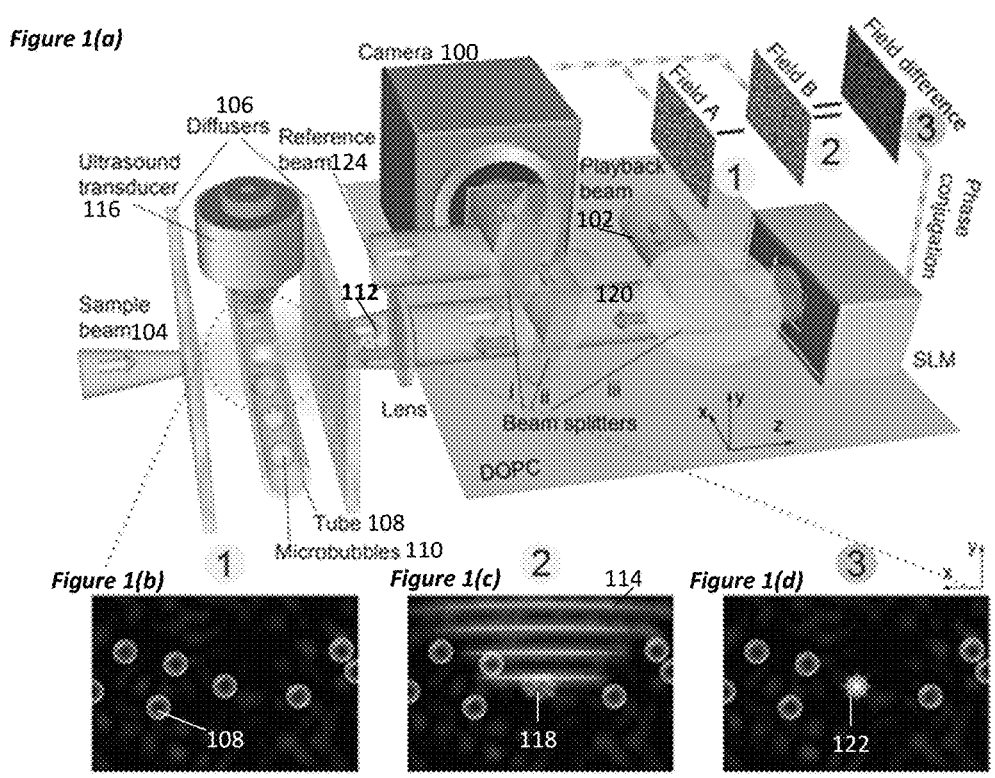

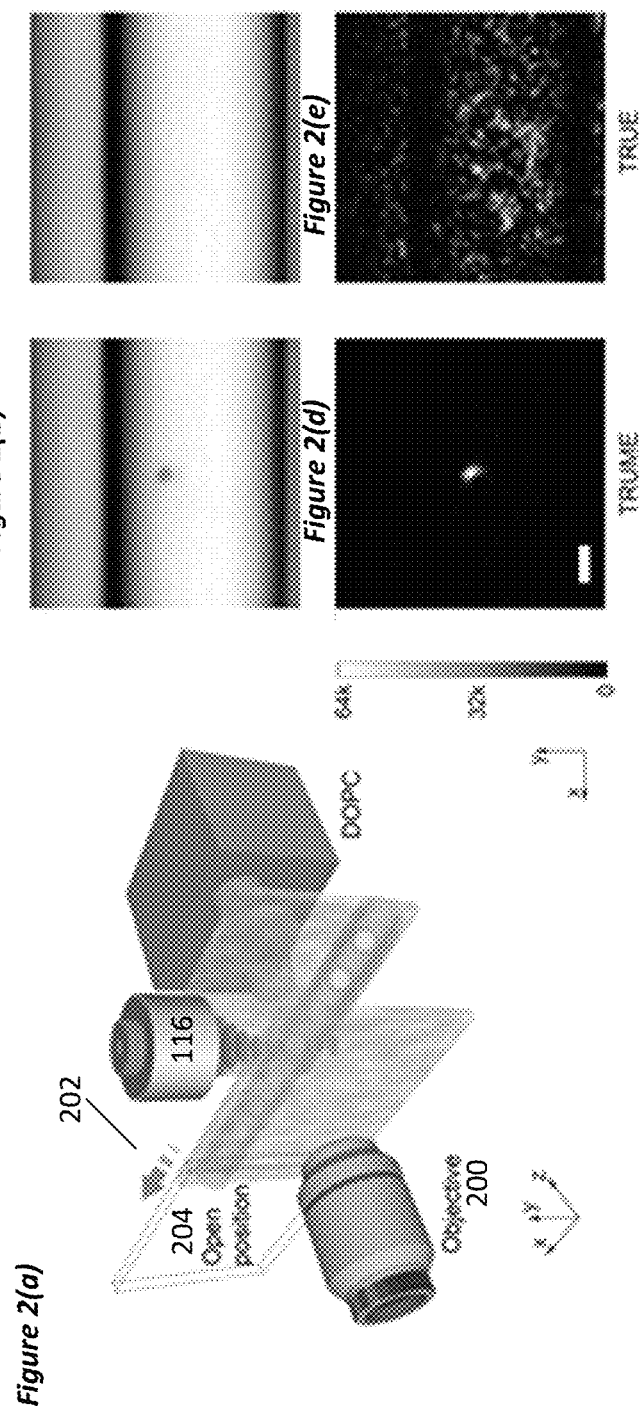

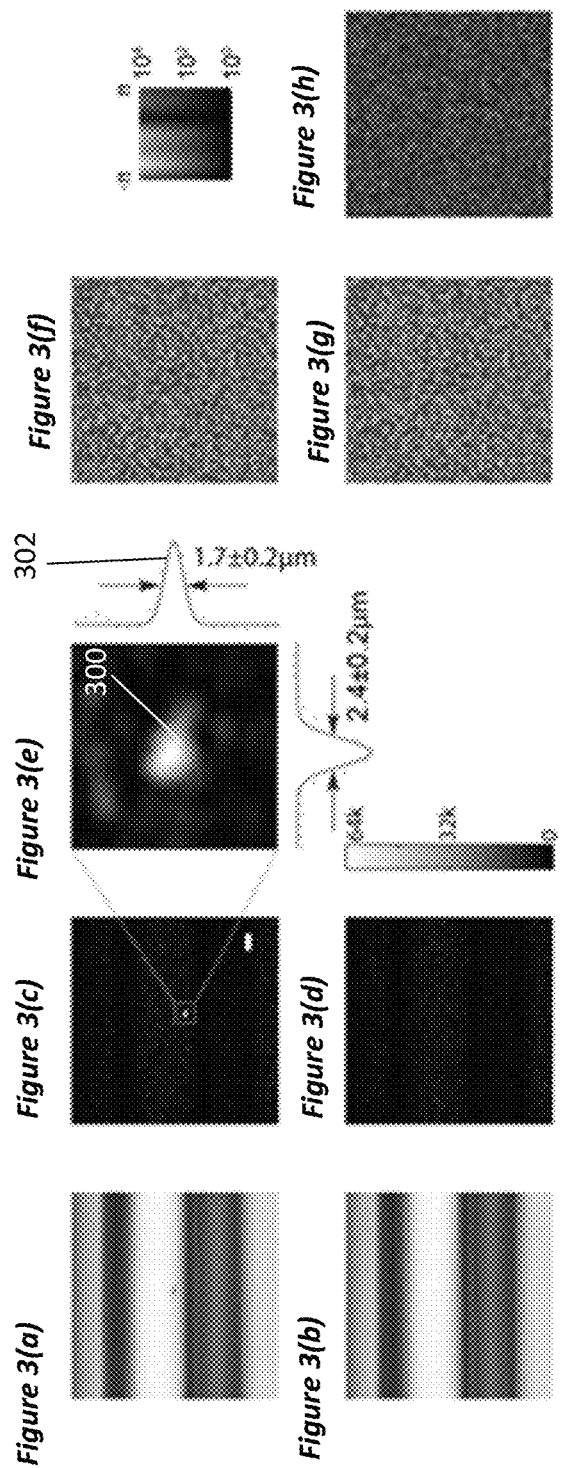

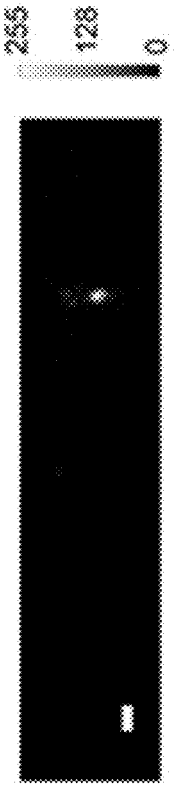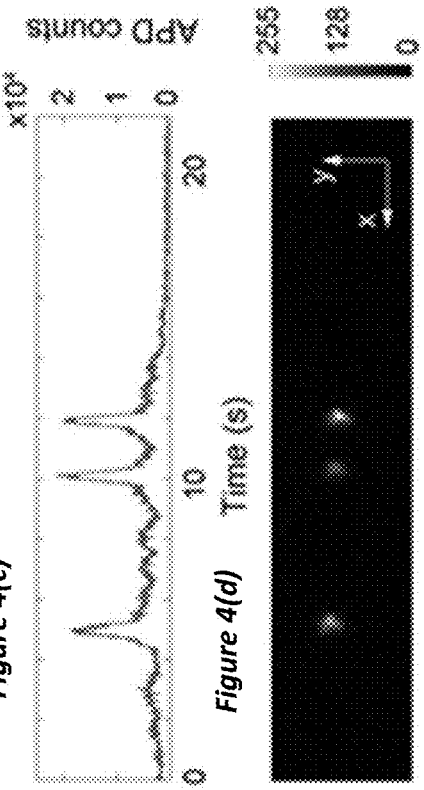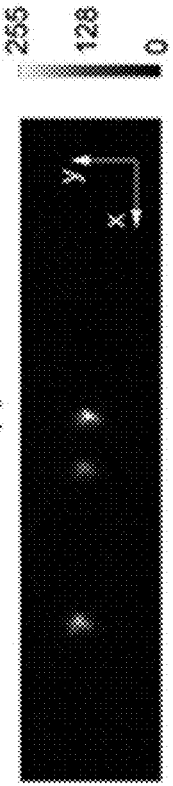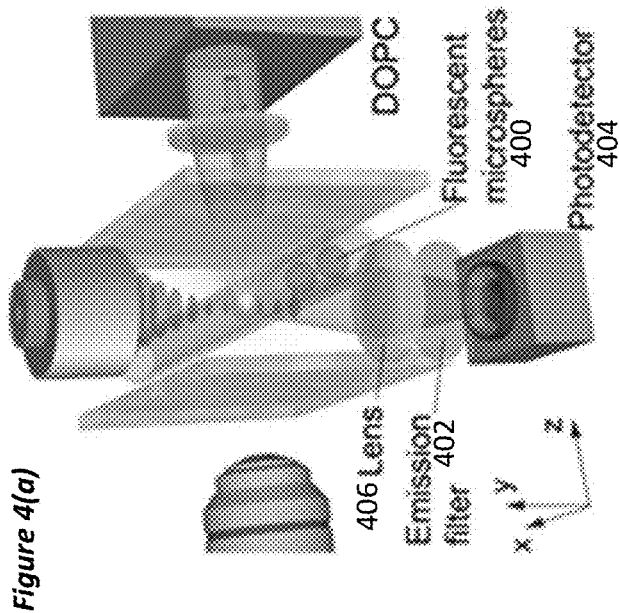
*Figure 4(a)*
*Figure 4(b)*
*Figure 4(c)*
*Figure 4(d)*

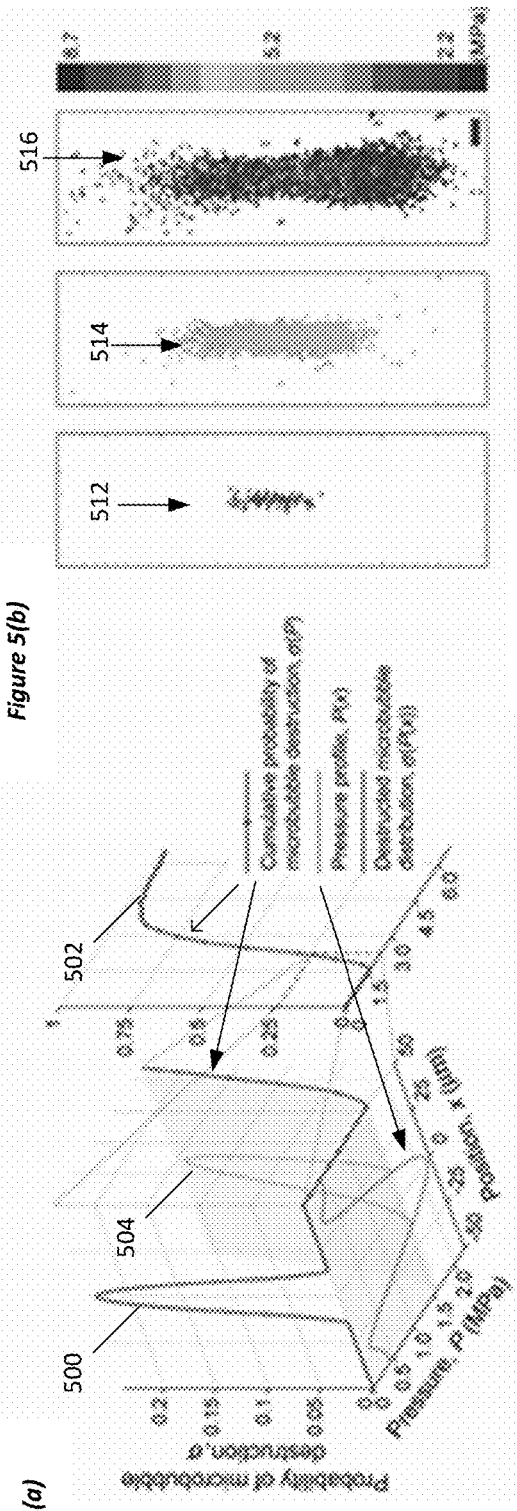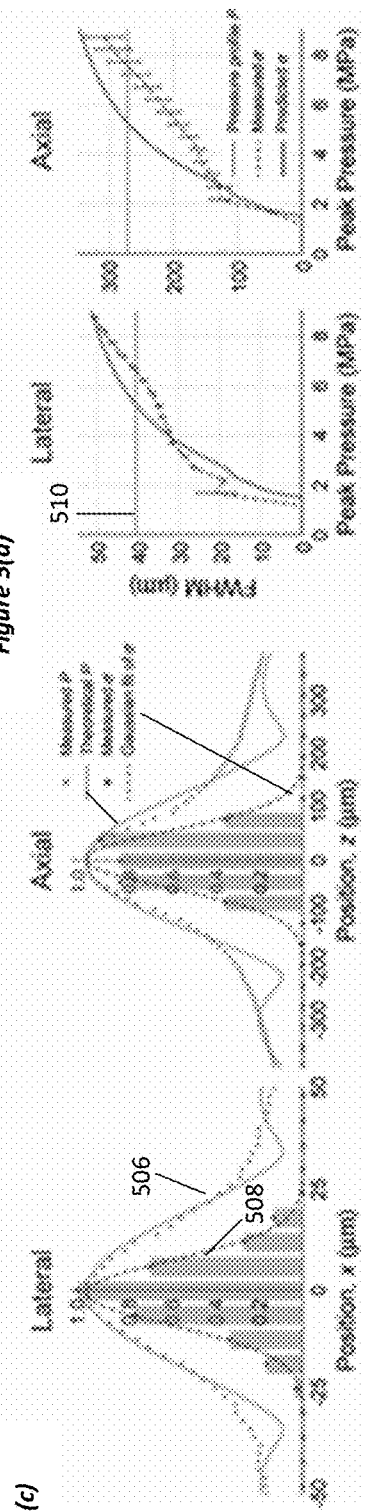
Figure 5(a)
Figure 5(b)
Figure 5(c)
Figure 5(d)

OPTICAL FOCUSING INSIDE SCATTERING MEDIA WITH TIME-REVERSED ULTRASOUND MICROBUBBLE ENCODED (TRUME) LIGHT

CROSS REFERENCE TO RELATED APPLICATIONS

This application claims the benefit under 35 U.S.C. Section 119(e) of co-pending and commonly-assigned U.S. Provisional Patent Application Ser. No. 62/174,858, filed on Jun. 12, 2015, by Haowen Ruan, Mooseok Jang, Changhuei Yang, and Daifa Wang, entitled "OPTICAL FOCUSING INSIDE SCATTERING MEDIA WITH TIME-REVERSED ULTRASOUND MICROBUBBLE ENCODED (TUBE) LIGHT," CIT-7212-P;

which application is incorporated by reference herein.

This application is related to the following co-pending and commonly-assigned patent applications, which applications are incorporated by reference herein:

U.S. Utility patent application Ser. No. 14/631,684 filed on Feb. 25, 2015, by Benjamin Judkewitz, Haojiang Zhou, and Changhuei Yang, entitled "DIGITAL PHASE CONJUGATION USING MOVING TARGET AS GUIDE STAR," which application claims the benefit under 35 USC Section 119(e) of U.S. Provisional Patent Application Ser. No. 61/944,368, filed on Feb. 25, 2014, by Benjamin Judkewitz, Haojiang Zhou, and Changhuei Yang, entitled "DIGITAL PHASE CONJUGATION USING MOVING TARGET AS GUIDE STAR;"

U.S. Provisional patent application Ser. No. 14/070,045, filed on Nov. 1, 2013, by Benjamin Judkewitz, Ying Min Wang, Roarke Horstmeyer, and Changhuei Yang, entitled "TIME-REVERSAL OF VARIANCE ENCODED LIGHT," now U.S. Pat. No. 9,354,166 issued May 31, 2016, which application claims the benefit under 35 USC 119(e) of U.S. Provisional Patent Application Ser. No. 61/721,325, filed on Nov. 1, 2012, by Benjamin Judkewitz, Ying Min Wang, Roarke Horstmeyer, and Changhuei Yang, entitled "TIME-REVERSAL OF VARIANCE ENCODED LIGHT;"

U.S. Utility patent application Ser. No. 13/851,901, filed on Mar. 27, 2013, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT," now U.S. Pat. No. 9,313,423 issued Apr. 12, 2016, which application claims the benefit under 35 U.S.C. Section 119(e) of U.S. Provisional Patent Application Ser. No. 61/616,347, filed on Mar. 27, 2012, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT;"

U.S. Utility patent application Ser. No. 12/886,320, filed on Sep. 20, 2010, by Zahid Yaqoob, Emily McDowell and Changhuei Yang, entitled "OPTICAL PHASE PROCESSING IN A SCATTERING MEDIUM," now U.S. Pat. No. 8,525,998 issued Sep. 3, 2013, which application is a divisional of U.S. Utility patent application Ser. No. 11/868,394, filed on Oct. 5, 2007, by Zahid Yaqoob, Emily McDowell and Changhuei Yang, entitled "TURBIDITY ELIMINATION USING OPTICAL PHASE CONJUGATION AND ITS APPLICATIONS," which application claims priority under 35 U.S.C. § 119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS;"

U.S. patent application Ser. No. 12/943,857, filed on Nov. 10, 2010, by Changhuei Yang and Meng Cui, entitled "TURBIDITY SUPPRESSION BY OPTICAL PHASE CONJUGATION USING A SPATIAL LIGHT MODULATOR," now U.S. Pat. No. 8,717,574 issued May 6, 2014, which application claims the benefit under 35 U.S.C. § 119(e) of the following co-pending and commonly-assigned U.S. provisional patent applications, which are incorporated by reference herein:

a. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES;"

b. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION;"

c. Provisional Patent Application Ser. No. 61/376,202, filed on Aug. 23, 2010, by Meng Cui and Changhuei Yang, entitled "OPTICAL PHASE CONJUGATION 4PI MICROSCOPE;" and d. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY;"

U.S. Utility application Ser. No. 12/943,841, filed on Nov. 10, 2010, by Meng Cui, Ying Min Wang, Changhuei Yang and Charles DiMarzio, entitled "ACOUSTIC ASSISTED PHASE CONJUGATE OPTICAL TOMOGRAPHY," which application claims priority under 35 U.S.C. § 119(e) to co-pending and commonly-assigned U.S. Provisional Application Ser. No. 61/355,328, filed on Jun. 16, 2010, by Meng Cui, Ying Min Wang, and Changhuei Yang, entitled "ACOUSTIC ASSISTED PHASE CONJUGATE OPTICAL TOMOGRAPHY;" U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES;" U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION;" and U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE;" and U.S. Utility application Ser. No. 13/157,194, filed on Jun. 9, 2011, by Meng Cui, Ying Min Wang, and Changhuei Yang, entitled "ITERATIVE TIME-REVERSAL ENHANCED TRANSMISSION SOLVING APPROACH," which application claims the benefit under 35 U.S.C. § 119(e) of Provisional Application Serial No. 61/355,326, filed on June 16, 2010, by Meng Cui, Ying Min Wang, and Changhuei Yang, entitled "ITERATIVE TIME-REVERSAL ENHANCED TRANSMISSION SOLVING APPROACH,".

STATEMENT REGARDING FEDERALLY SPONSORED RESEARCH AND DEVELOPMENT

This invention was made with government support under Grant No. OD007307 & NS090577 awarded by the National Institutes of Health. The government has certain rights in the invention.

BACKGROUND OF THE INVENTION

1. Field of the Invention

This invention relates to methods and devices for irradiating scattering media.

2. Description of the Related Art (Note: This application references a number of different publications as indicated throughout the specification by one or more reference numbers in superscripts, e.g., [x]. A list of these different publications ordered according to these reference numbers can be found below in the section entitled "References." Each of these publications is incorporated by reference herein.)

Creating an optical focus inside scattering medium, such as biological tissue, has a great potential in various applications. However, optical scattering, as a dominant light matter interaction in the biological tissues, poses a very significant challenge. Recent developed wavefront shaping techniques have begun to address this[1-4] by exploiting the deterministic and time-symmetric nature of scattering. Focusing of light through scattering media has been realized by iterative optimization method[2,5], optical phase conjugation (OPC)[6,7], or direct large scale measurement of the transmission matrix [8-10].

To focus light within a scattering medium requires an additional factor—a 'guidestar' mechanism to provide feedback or tagging, in order for the techniques to arrive at the right optical wavefront solution. Examples of guidestars include second harmonic generation[11], fluorescence[12,13] and kinetic[14,15] targets. While these guidestars allow light focusing to their physical locations, these techniques fundamentally lack addressability if dense and randomly distributed guidestars are present.

Alternatively, ultrasound-assisted techniques, such as photoacoustic-guided[10,16-18] and time-reversed ultrasonically-encoded (TRUE)[19-21] optical focusing techniques, employ a focused ultrasound beam as a virtual guidestar that can confine the focus at a freely addressable position. While TRUE has a speed advantage over the photoacoustic approach, the TRUE guidestar is generally weak. In the lossless case, typically ~1% of the probe light field that passes through the ultrasound focus is tagged[22,23]. Moreover, the resolution achieved is limited by the ultrasound focus size. Although more advanced TRUE techniques—iterative TRUE (iTRUE)[24-26] and time reversal of variance-encoded light (TROVE)[27], are able to break this resolution barrier, they achieve this at the expense of time. For practical biological applications with tight time constraints, efficient and fast techniques are highly desired.

SUMMARY OF THE INVENTION

Focusing light inside scattering media in a freely addressable fashion is challenging, as the wavefront of the scattered light is highly disordered. Recently developed ultrasound-guided wavefront shaping methods are addressing this challenge, albeit with relatively low modulation efficiency and resolution limitations.

One or more embodiments of the invention overcome these limitations and disclose a method for irradiating scattering medium, including modifying a particle's response to electromagnetic radiation irradiating the particle in a scattering medium, wherein the electromagnetic radiation is scattered by the scattering medium, and modulated by the modifying, into scattered electromagnetic radiation comprising a scattered field; forming a phase conjugate field, wherein the phase conjugate field is a phase conjugate of the scattered field; and irradiating the scattering medium with the phase conjugate field, wherein the phase conjugate field forms a focus at a target defined by the particle.

In one or more embodiments, the modifying comprises interacting the particle with least one field selected from an electric field, a magnetic field, an electromagnetic field, and an acoustic field (e.g., ultrasound).

In one or more embodiments, the response is a nonlinear response controlled during the modifying to tailor a size of the focus. For example, the modifying can comprises controlling a pressure applied to the particle comprising a bubble.

In one or more embodiments, the new technique comprises time-reversed ultrasound microbubble encoded (TRUME) optical focusing, which is able to focus light with improved efficiency and sub-ultrasound wavelength resolution. This method ultrasonically destructs microbubbles, and measures the wavefront change to compute and render a suitable time-reversed wavefront solution for focusing. The present invention demonstrates that the TRUME technique can create an optical focus at the site of the bubble destruction with a size of ~2 μm. Due to the nonlinear pressure-to-destruction response, TRUME technique can break the addressable focus resolution barrier imposed by the ultrasound focus. The present invention further experimentally demonstrates an addressable focus resolution is improved by 2-fold in a microbubble aggregate target.

One or more embodiments of the invention further disclose an apparatus for irradiating a scattering medium, comprising a field source electromagnetically connected to a support, wherein a field emitted from the field source modifies a particle's response to electromagnetic radiation irradiating the particle in a scattering medium on the support; a phase conjugate mirror electromagnetically connected to the support; a laser electromagnetically connected to the phase conjugate mirror, wherein: output electromagnetic radiation outputted from the laser interacts with the phase conjugate mirror to form the output electromagnetic radiation comprising the phase conjugate field that forms a focus at a target defined by the particle.

In one or more embodiments, the phase conjugate mirror comprises a photorefractive crystal or photorefractive film, the photorefractive crystal or photorefractive film recording the scattered field in an interference pattern formed in the photorefractive crystal or photorefractive film.

In one or more embodiments, the apparatus further comprises a camera capable of measuring an interference pattern between a reference field and the scattered field; one or more processors connected to the camera, the one or more processors capable of calculating the scattered field from the interference pattern; the phase conjugate mirror comprising a spatial light modulator (SLM) aligned with the camera; and one or more processors connected to the spatial light modulator (SLM), the one or more processors connected to the spatial light modulator capable of calculating the phase conjugate field from the scattered field; and wherein the SLM programmed with the phase conjugate field forms the output electromagnetic radiation.

Applications of one or more embodiments of the invention include using the focus to image the scattering medium comprising biological cells, wherein the focus is formed at a depth of at least 1 cm below a surface of the scattering medium, using the focus to count the biological cells, or using the focus to excite a chemical composition at the target or heats the target comprising diseased cells, without damaging a surface of the biological tissue.

BRIEF DESCRIPTION OF THE DRAWINGS

Referring now to the drawings in which like reference numbers represent corresponding parts throughout:

FIG. 1(a), FIG. 1(b), FIG. 1(c), and FIG. 1(d) illustrate the principle of a TRUME technique, according to one or more embodiments of the present invention. FIG. 1(a) is an illustration of the experimental setup showing the microbubbles perfuse inside an acrylic tube, which is sandwiched between two diffusers, and a Digital Optical Phase Conjugation (DOPC) system is used as a phase conjugation mirror to time-reverse the light back to the sample. FIGS. 1(b)-(d) are an illustration of the TRUME optical focusing technique in 3 steps, wherein at the first step, the camera of the DOPC system captures a transmitted optical field (Field A) before applying ultrasound to the sample (FIG. 1(b)), ultrasound bursts are then used to destruct the targeted microbubble (FIG. 1(c)), resulting in a different optical field (Field B), and at the last step, the difference between two fields is calculated, yielding an optical field from the destroyed microbubble, and the conjugated phase of the resulting field is then sent to the Spatial Light Modulator (SLM) to create a playback beam that focuses at the position of the destroyed microbubble (FIG. 1(d)).

FIG. 2(a), FIG. 2(b), FIG. 2(c), FIG. 2(d), and FIG. 2(e) illustrate visualization of the target plane, according to one or more embodiments of the present invention. FIG. 2(a) is an illustration of the observation setup, wherein the front diffuser was shifted to the open position before and after TRUME implementation for direct visualization, and a 10× microscope system was used to observe the targeted plane of the sample. FIG. 2(b) and FIG. 2(c) show images of a microbubble before and after applying ultrasound. FIG. 2(d) shows the optical focus created at the position where microbubble was destroyed. FIG. 2(e) shows focusing results of the TRUE technique. Scale bars: 50 micrometers (μm).

FIG. 3(a), FIG. 3(b), FIG. 3(c), FIG. 3(d), FIG. 3(e), FIG. 3(f), and FIG. 3(g) illustrate optical focusing in 2-mm deep chicken tissue, according to one or more embodiments of the present invention, wherein two pieces of 2-mm thick chicken tissues were used as diffusers. FIG. 3(a) shows a microbubble in a tube before destruction. FIG. 3(b) shows inside the tube after destruction of the microbubble. FIG. 3(c) shows a light focus was created at the position of the destroyed microbubble (PBR ~23). FIG. 3(d) shows the optical focus vanished as the SLM shifts 10 pixels in both x and y directions. FIG. 3(e) shows a 10× zoom-in image of the optical focus with quantified resolution. FIG. 3(f), FIG. 3(g) show the central part (200 pixels by 200 pixels) of the optical fields captured before (FIG. 3(f)) and after (FIG. 3(g)) the destruction of the microbubble. FIG. 3(h) shows the difference of the fields in FIG. 3(f) and FIG. 3(g). Scale bar: 10 μm.

FIG. 4(a), FIG. 4(b), FIG. 4(c), and FIG. 4(d) illustrate demonstration of flow stream monitoring through scattering samples, according to one or more embodiments of the present invention. FIG. 4(a) is an illustration of the experimental setup. An SPCM was used to detect the excited fluorescence through the fluorescence filter. FIG. 4(b) shows a light focus was created by using TRUME. FIG. 4(c) shows photon counts recorded by the SPCM as the optical focus probed the flowing microspheres. FIG. 4(d) shows the image of the fluorescent microspheres after passing through the optical focus in the x direction. Scale bar: 10 μm.

FIG. 5(a), FIG. 5(b), FIG. 5(c), and FIG. 5(d) illustrate addressable focus resolution improvement by exploiting nonlinear microbubble destruction, according to one or more embodiments of the present invention. FIG. 5(a) illustrates a calculation of microbubble destruction probability distribution as a function of position (500, blue) based on the measured cumulative distribution function of the microbubble destruction σ(P) (502, red) and the theoretical ultrasound pressure profile P(x) (504, green). FIG. 5(b) illustrates two-dimensional distribution map of TRUME foci as a function of pressure levels. FIG. 5(c) illustrates comparison of the TRUME focus probability distribution (histograms) and the ultrasound pressure profile (506, green) in both lateral (left) and axial (right) directions. The histograms were calculated from the focus map of the lower pressure level group (left figure in FIG. 5(b)). A Gaussian function was fitted to each histogram. FIG. 5(d) shows the theoretical (e.g. full width at half maximum (FWHM) of the blue curve 500 in FIG. 5(a) and experimental (e.g. FWHM of the blue curve 508 in FIG. 5(c)) TRUME addressable focus resolution as a function of pressure. Green lines 510 mark the FWHM of the ultrasound profile. Error bar indicates 95% confidence bound. Scale bar in FIG. 5(b): 50 μm.

DETAILED DESCRIPTION OF THE INVENTION

Figure 6:
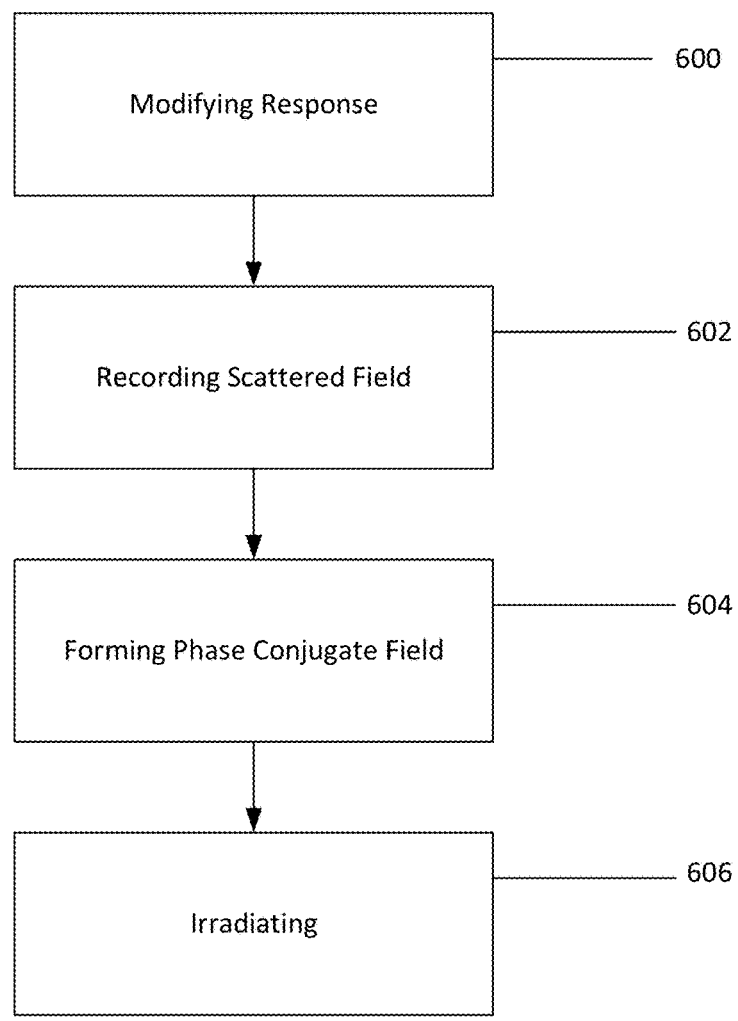
FIG. 6 illustrates a method of irradiating a scattering medium according to one or more embodiments of the invention.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

One or more embodiments of the present invention disclose a high resolution, deep tissue optical focusing technique termed a Time-reversed Ultrasound Microbubble Encoded (TRUME) optical focusing technique. Microbubbles have been widely used in ultrasonic imaging as ultrasound contrast agents because they generate stronger echoes and nonlinear signals than the surrounding tissues[28,29]. The applications of microbubbles in optical imaging are emerging, with successful demonstrations of ultrasound modulated optical imaging inside scattering media[30-32]. As they can be modified to bind to selected biomarkers, microbubbles also have promising applications in functional imaging and therapeutic applications[28].

One or more embodiments of the present invention demonstrate that the selective nonlinear destruction of microbubbles with focused ultrasound beams can serve as effective, highly localized and freely-addressable guidestars. In brief, TRUME works by measuring the scattered optical fields before and after the ultrasonic destruction of the microbubble. Subsequently, by playing back the phase conjugate of the difference of these two fields, TRUME can generate a focus at the location of the destroyed microbubble. Although multiple foci could be created at the same time when multiple microbubbles are present within the original ultrasound focus, one or more embodiments of the present invention show that careful selection of the ultrasound pressure can lead to destruction of microbubbles in an addressable volume that is sub-ultrasound focus in size. This is because of the highly nonlinear nature of the pressure-to-destruction response curve for the microbubbles. This technique combines the advantages of both physical and virtual guidestars to provide an efficient and fast optical focusing ability.

TRUME System Example

A TRUME demonstration system according to one or more embodiments of the present invention uses a digital optical phase conjugation (DOPC) system as its wavefront recording and playback engine[7,25] (FIG. 1(a)). In the recording phase, the scattered field from the sample is recorded by the camera 100 of the DOPC system. In the playback step, a suitable pattern is displayed on the spatial light modulator (SLM) and a collimated 'blank' playback beam 102 imprints off it to form the playback light field. Precise alignment of the camera 100 and SLM allows high fidelity phase conjugate playback of the recorded field. Experimentally, this DOPC system is able to control ~$10^5$ optical modes simultaneously[33].

FIG. 1(a) illustrates TRUME demonstrated in a transmission geometry, in which a sample beam 104 transmits through the sample (comprising diffusers 106, tube 108, and microbubbles 110) in the z direction and part of the scattered light 112 is measured by the camera 100 on other side of the sample. An ultrasound beam 114 from ultrasound transducer 116 is focused on the microbubbles 108 embedded between two diffusers through water coupling. The operation procedure of TRUME can be divided into three steps (1)-(3). First, an optical field (Field A) is measured by the camera (FIG. 1(b), step (1)) through a 4-phase shifting based digital holography method[34]. In the second step (FIG. 1(c), step (2)), ultrasound is applied to destroy the targeted microbubble 118, immediately followed by the measurement of a second optical field (Field B). The difference of the fields (Field A–Field B) is the scattered field solution associated with the microbubble. The DOPC system computes this difference field and plays back a phase conjugate copy 120. Since the difference field primarily contains information from the microbubble only, the conjugated beam focuses to the position 122 of the destroyed microbubble (FIG. 1(d), step (3)). The DOPC further comprises beamsplitters (i), (ii) to combine the scattered light 112 with a reference beam 124 to form an interference pattern on the camera 100. Beamsplitter (iii) is used to reflect the playback beam 102 off the SLM to form the phase conjugate copy 120.

TRUME shares the same mathematical framework as a kinetic objects based technique[14,15]. The optical field on the target plane $E_t$ can be decomposed into a microbubble diffracted field $E_m$ and a background field $E_b$, which describes the field after microbubble destruction, wherein $E_t = E_m + E_b$. Since the camera and SLM contain discrete components, it is convenient to discretise $E_m$ and $E_b$ as column vectors with n complex elements, with each component mapping to an optical mode on the two-dimensional target plane. This target field can then be connected to the field on the measurement plane through a matrix equation $E_t' = T(E_m = E_b)$, where T is a m×n matrix describing the scattering medium, $E_t'$ is a column vector of m elements with each element mapping to an optical mode on the two-dimensional measurement plane. Similarly, the field measured after microbubble destruction can be given by $E_b' = TE_b$. The difference field on the measurement plane is then calculated:

$$E_d' = E_t' - E_b' \quad (1)$$
$$= T(E_m + E_b) - TE_b$$
$$= TE_m.$$

As shown in the above equation, the impact of the background field on the measurement plane is effectively removed by field subtraction, resulting in a field that appears to be scattered from the microbubbles only. Finally, the difference field in Equation (1) is conjugated and played back through the scattering medium. Assuming time-reversal symmetry, we may express playback as a multiplication with T from the left with the conjugate transpose of the difference field. Therefore, the playback field $E_p$ on the target plane is given by $$E_p = E_d'^* T \quad (2)$$
$$= (TE_m)^* T$$
$$= E_m^* T^* T$$
$$\approx E_m^*.$$

Here, minimal absorption within the sample is assumed to apply the approximation $T^*T \approx I$, in which I is an identity matrix. Therefore, the playback light effectively cancels out the random transmission matrix and refocuses to the location of microbubble destruction.

Example of Visualization and Efficiency Characterization of the Focus

In order to demonstrate the TRUME focusing results, the target plane is directly visualized using a 10× microscope system (objective 200, see Methods) before and after the TRUME procedure. In this experiment, the front diffuser 104 is shifted 202 along the x direction (to the open position 204 as shown in FIG. 2(a)) to expose the target plane during the focusing phase. The target sample here comprises microbubbles embedded in agarose gel within an acrylic capillary tube (see Methods) as shown in FIG. 2(b). Immediately after measuring the first optical field, a 20 MHz focused ultrasound beam was used to destruct the microbubbles, followed by the measurement of the second field. The target plane is then imaged again to confirm the destruction of the microbubble (FIG. 2(c)) and the focus created at the position of destroyed microbubble is directly visualized (FIG. 2(d)). As shown in FIG. 2(d), the size of the focus matches the size of the microbubble as shown in FIG. 2(b). The measured peak intensity to background intensity ratio (PBR) of the TRUME focus in FIG. 2(d) is ~510. Theoretically, the PBR is estimated by PBR=[($\pi$/4)/(N−1)+1]/M for phase only modulation[20,35], where N is the number of controllable modes and M is the number of optical modes at the focus. In our case, the size of the microbubble is in the same order as the speckle, which would result in PBR ~$10^5$. Experimentally, the measured PBR is around two orders of magnitude lower than the theoretical value mainly due to the effect of shot noise and background field fluctuation between two measurements.

For comparison, the focusing profile using TRUE (FIG. 2(e)) was also measured. The PBR of the TRUME focus is around two orders of magnitude higher than that of TRUE (PBR=18 2 in FIG. 2(e)). This is because the TRUME further confines the number of encoded optical modes and has stronger modulation efficiency per mode.

The modulation efficiency in a clear sample (see Supplementary Information[47]) was separately measured, finding that the proportion of light passing through the ultrasound focus (2 MPa peak pressure) and that is modulated is ~1%. In comparison, the proportion of light passing through the location of the bubble and that is modulated by the bubble destruction reaches ~25%. This large difference in modulation efficiency is primarily the reason why the TRUME guidestar particularly strong.

Example of Deep Tissue Optical Focusing

To study the performance of the TRUME in focusing through biological tissues, two pieces of 2-mm thick biological tissues were used as optical diffusers. The experimental setup was based on that shown in FIG. 2(a). The images of the microbubble before and after destruction are shown in FIGS. 3(a) and 3(b), respectively. An optical focus 300 (FIG. 3(c), (e)) was created using TRUME, with PBR of ~23. To characterize the size of the focus, a Gaussian profile 302 was fitted to the one-dimensional data through the centre of the focus in the x and y directions. The result shows that the full width at half maximum (FWHM) of the focus (FIG. 3€ ) is 2.4±0.2 µm in the x direction and 1.7±0.2 µm in the y direction (95% confidence bound). To confirm that this optical focus was created due to optical phase conjugation, the SLM pixel in both x and y directions were shifted by 10 pixels. As shown in FIG. 3(d), the optical focus vanished as expected. The optical fields measured before and after microbubble destruction, as well as the subtracted field, are shown in FIGS. 3(f)-3(h), respectively.

Demonstration Example of Flow Stream Monitoring

One of the potential applications of TRUME is cytometry behind the scattering media, as microbubbles are currently in use as contrast agents in blood circulation ultrasound imaging[28]. To demonstrate the proof of concept here (FIG. 4(a)), fluorescent microspheres 400 (4 µm) and microbubbles were mixed in 1× phosphate buffered saline (PBS) and pumped the solution through an acrylic tube (see Methods). An optical focus was first created as shown in FIG. 4(b) by implementing TRUME on a microbubble at the target location. Fluorophores that subsequently flowed across the focus would interact with the focused light spot and emit fluorescence. The fluorescence was filtered with an emission filter 402 and detected by a single photon counting module (SPCM or photodetector 404, see Methods) using a lens 406, with its output signal shown in FIG. 4(c). After counting, the front diffuser was shifted to the open position and the fluorescent microspheres were imaged with an emission filter for verification (FIG. 4(d)). The agreement of the results positively validates this proof-of-concept.

Addressable Focus Resolution Improvement with Non-linearity of Microbubble Destruction.

When microbubbles are dense, multiple foci could be created by TRUME (e.g. FIG. 2(g)) because a typical ultrasound focus is one to two orders of magnitude larger than the microbubble. In this scenario, TRUME will generate an optical focus that can be significantly broader than the focus discussed thus far. To distinguish the two foci, the term addressable focus is used to refer to the achievable TRUME focus in the scenario where microbubbles are dense.

The addressable focus size is determined by the pressure-to-destruction response of the bubbles. Interestingly, the probability of microbubble destruction varies nonlinearly as a function of pressure. In the ideal case where all microbubbles have the same destruction threshold, one can set the ultrasound pressure right at the threshold so that only the microbubble at the centre of the ultrasound focus can be destroyed and obtain addressable focus size that is equal to the single bubble TRUME focus size. In practice, the actual pressure-to-destruction response curve is not a simple step function. Nevertheless, the more nonlinear the response curve is, the sharper the addressable focus that can be achieved with TRUME.

To better characterize the pressure-to-destruction response and determine the TRUME addressable focus resolution achievable with the system according to one or more embodiments of the invention, the cumulative distribution function of the microbubble destruction $\sigma$(P) was measured by counting the number of microbubble destroyed as a function of pressure. As shown in FIG. 5(a) (502, red), the cumulative distribution function reveals a strong non-linear relationship between destruction probability and pressure. Given a focused ultrasound profile P(x) (FIG. 5(a), 504, green, see also Methods), it was possible to calculate the microbubble destruction probability as a function of positon $\sigma$(P(x)) (FIG. 5(a), blue 500), which predicts the addressable focus resolution of TRUME. The resulting profile is significantly narrower than the ultrasound pressure profile, implying that the nonlinear relationship would effectively improve the addressable focus resolution of TRUME.

To experimentally confirm the improvement of addressable focus resolution in TRUME with this nonlinear effect, TRUME was performed on a thin microbubble sheet (see Methods) to visualize the distribution of the foci as ultrasound pressure increases. The microbubble sheet was positioned between, and parallel to, the diffusers. In order to cover the entire ultrasound focus (−6 dB) with the current observation system and further improve the resolution, a 45 MHz, high numeric-aperture ultrasound beam was used with a measured beam diameter and focal zone (−6 dB) of ~40 µm and ~270 µm respectively (see Methods) in this experiment. The ultrasound beam was aligned to the microbubble sheet by maximizing the amplitude of the echo received from the focus. TRUME was performed with 18 levels of ultrasound pressure in ascendant order (linearly from 0.15 to 8.7 MPa), resulting in 18 conjugated phase maps. These phase maps were then played back in sequence and the focus patterns were captured using the observation system in the setup. To collect meaningful statistics, this process was repeated 135 times at different regions of the microbubble sheet. The position information of each focus was extracted using a watershed algorithm (see Methods) and accumulated from 135 sets of data as shown in FIG. 5(b), where foci are displayed in 3 pressure groups (lower pressure 512, medium pressure 514 (~5 MPa), and higher pressure 516 (~8 MPa)).

The profile of the foci broadens as the ultrasound pressure becomes higher, confirming the nonlinearity effect in TRUME.

To quantify the addressable focus resolution improvement with nonlinear effect in the lower pressure group 512 (~2 MPa) where microbubbles start to collapse, the histograms of the foci in both lateral and axial directions were calculated and fitted a Gaussian profile to each histogram (FIG. 5(c)). The ultrasound pressure profiles were also measured, which show good match with the theoretical calculation in both directions (see Methods). The FWHM of the Gaussian profile fitted to the histogram in the lateral direction is 19 µm, while that of theoretical ultrasound focus is 40 µm. A significant resolution improvement is also observed in the axial direction, where these two numbers are 130 µm and 270 µm, respectively. The effect of ultrasound pressure on the nonlinearity induced resolution improvement was further studied by calculating of the FWHMs of both theoretical microbubble destruction distribution (e.g. blue curve 500 in FIG. 5(a)) and TRUME focus histogram profiles (e.g. blue curve 508 in FIG. 5(c)) at various pressure levels. As shown in FIG. 5(d), the experimental FWHM matches the theoretical prediction in both lateral and axial directions, further confirming that TRUME achieves higher addressable focus resolution than that defined by the ultrasound focus, by utilizing the nonlinear pressure-to-destruction response. The discrepancy between these two curves is attributable to variations of the samples.

Discussion

Combining the advantages of a physical and a virtual guidestar, TRUME is able to focus light to a size of ~2 µm in deep tissue with a targeting region selected by the ultrasound focus. One or more embodiments of the present invention demonstrate the addressable focus resolution of TRUME can be improved by a factor of ~2 from the ultrasound defined resolution. As this method simply requires two measurements and no iterations, it is intrinsically fast and a good match with in-vivo applications. The factors that affect the TRUME performance and the potential applications of TRUME are outlined and discussed in this section.

The size of an individual focus depends on that of the microbubble which is typically on a micrometre scale, ~10-fold smaller than a TRUE focus. Although the ultrasound focus could cover multiple microbubbles, TRUME further confines the targeting range by taking the advantage of the nonlinear relationship between destruction population and ultrasound pressure. The addressable focus resolution improvement was largely limited by the broad size distribution of the microbubbles, and thus can be enhanced by using more uniform microbubbles, which can be obtained by using, for example, separation techniques[36] or methods based on established protocols[37,38]. On the other hand, multi-focusing can be desirable in some potential applications where microbubbles themselves have selectivity (e.g. binding to certain disease markers).

The PBR of TRUME with a ground glass diffuser sample (~510) is ~100-fold higher than that of TRUE obtained in the same setup as shown in FIG. 2(a). This is because of two factors. First, the number of optical modes encoded by the TRUME is practically much smaller even when multiple microbubbles are present within the ultrasound focus. Second, the modulation efficiency of TRUME versus TRUE is much higher. In our experiment, it was found that ~25% of the light passing through the TRUME guidestar is modulated. In comparison, a TRUE guidestar with a local pressure of 2 MPa is only able to modulate ~1% of the light.

Taking the advantage of parallel field measurement, this DOPC based technique creates optical foci in hundreds of milliseconds (~280 ms in our experiments), a timescale short enough for ex-vivo or even some in-vivo biological applications[39]. It should be noted that no frame averaging was done for TRUME in all the experiments demonstrated in this disclosure. The operation speed is limited by the system frame rate, which can be improved by using a Field programmable Gate Array (FPGA) based system. An off-axis holography based field measurement or a binary phase measurement would further improve the system speed by reducing the number of frames needed for field measurement.

The time needed to destruct/destroy a microbubble depends on the mechanisms of microbubble destruction, which can be classified into fragmentation and diffusion[40]. Fragmentation occurs when ultrasound pressure is relatively high (typically >2 MPa) and the microbubble is destroyed within the timescale of microseconds, which is ideal for TRUME in terms of operation speed. However, if low ultrasound pressure is used, acoustic driven diffusion dominates the destruction mechanism. This process typically spans tens of microseconds, depending on the ultrasound parameters (pressure, frequency, cycles, etc.) and microbubbles properties such as size, shell material and encapsulated gas[40]. In the TRUME experiments demonstrated in this disclosure, the ultrasound duration was 28.6 ms (one camera frame period), within which incomplete gas dissolution was also observed under some circumstances such as low ultrasound pressure and large microbubble diameter (See Supplementary videos for comparison of rapid and slow microbubble destruction). This effect results in a size decrease rather than complete disappearance of the microbubble. Intriguingly, decreasing the size of the microbubble between capturing two optical fields also enables TRUME to create an optical focus at the targeted microbubble, because it shares the same effect as the complete destruction—inducing a difference between two optical fields.

Microbubbles are usually made with albumin or lipid, which stabilizes high molecular weight gas, such as perflutren. These microbubbles have been widely used as ultrasound contrast agents and proven for some applications in human bodies. The good biocompatibility of microbubble makes it a promising optical guidestar in the biological tissues. Besides ultrasonic imaging, microbubbles have promising applications in gene and drug delivery[41], where ultrasonic destruction of the microbubbles releases the therapeutic payload. Intriguingly, microbubbles can be targeted to regions of disease by surface conjugation of specific ligands or antibodies that bind to the disease markers[28]. Recently, genetically encoded gas nanostructure from microorganisms has been demonstrated to be a promising candidate for a molecular reporter[42]. All these applications imply that microbubbles have high specificity and selectivity, with which TRUME would enable precise optical mediation with drugs or cells or molecules. Example applications cover selective photo-thermal therapy for targeting tumour cells[43] and specific light delivery in optogenetics[44].

Method Example

Setup

The TRUME experiment was carried out in a custom-built setup. The schematic diagram of the setup is illustrated in Supplementary FIG. 1 in the Supplementary information[47]. A pulsed laser beam (532 nm wavelength, 7 ns pulse width, 20 kHz repetition rate, 7 mm coherent length) generated from a Q-switch laser (Navigator, Spectra-Physics, U.S.A.) was spilt into three beams: a sample beam, a reference beam and a playback beam. Both of the sample beam and the reference beam were shifted by 50 MHz using an acousto-optical modulator (AOM, AFM-502-A1, InstraAction, U.S.A.). The interference between the transmitted sample beam and reference beam was measured by a camera (PCO.edge, PCO, Germany) of the DOPC system. The playback beam was modulated with the conjugated phase of the subtracted field by an SLM (Pluto, Holoeye, Germany), which was precisely aligned to the camera through a beam splitter.

The 20 MHz ultrasound burst was generated by a transducer with a 13 mm focal length and 6.35 mm element diameter (V317, Olympus, U.S.A.), and the 45 MHz ultrasound burst was generated by a transducer that has a 6 mm focal length and 6.35 mm element diameter (nominal frequency at 50 MHz, calibrated peak frequency at 44.4 MHz, V3330, Olympus, U.S.A.). Both transducers were driven by a RF power amplifier (30 W1000B, Amplifier Research, U.S.A.).

To directly visualize the results, a custom-built microscope with a 20× objective (SLMPlan N, Olympus, Japan) and a tube lens of 10 mm focal length was used to image the target plane to a CCD camera (Stingray, Allied Vision Technologies, Germany). To demonstrate the cytometry application, the fluorescent signals were filtered by a 561 nm long-pass (LP02-561RE-25, Semrock, U.S.A.) and a 582/75 nm band-pass filter (FF01-582/75-25, Semrock) and detected by a SPCM (SPCM-AQRH-14, Perkinelmer, Canada).

Signal flow

The signal flow is shown in detail in Supplementary FIG. 2 in the Supplementary Information[47]. The sample beam and reference beam were modulated by 50 MHz signals generated from two channels of a function generator (AFG 3252, Tektronix, U.S.A.). The optical field transmitted through the sample was measured by the camera (exposure time: 20 ms, framerate: 35 fps) of the DOPC system using 4-phase shifting based digital holography[34]. The phase shifting was synchronised with the camera exposure by controlling signals from a data acquisition (DAQ) (PCI-6281, NI, U.S.A.). The ultrasound burst signal (10 cycles, 10 µs interval) was generated by another function generator (4065, BK Precision, U.S.A.) and time-gated (28.6 ms) by the DAQ.

Sample Preparation

The microbubbles (Optison, GE health care, U.S.A.) was diluted to 10% (v/v %) in 1% (w/w %) agarose gel in aqueous phase (for visualization of the focus) or 1× PBS (for demonstration of application in cytometry and Deep tissue optical focusing) and perfused in an acrylic capillary tube (ID 50, OD 100, Paradigm Optics, U.S.A.), which was positioned inside a clear polystyrene cuvette. 10% Polyacrylamide gel was used to fill the space in the cuvette to secure the capillary tube. Two diffusers (10×10 mm 220 grit ground glass, Edmund Optics, U.S.A.) were placed outside the cuvette in parallel with ~10 mm distance in between. The microbubble sheet was ~20 µm thick and embedded in two blocks of agarose gel with dimensions of 10 mm (x)×10 mm (y)×3 mm (z). In the cytometry experiment, fluorescent microspheres with 4 µm diameter (FluoSpheres 580/605, Life Science, U.S.A.) were used as targets. In the ex-vivo tissue experiment, fresh chicken breast tissues were used as diffusers. For each tissue diffuser, a piece of 2-mm thick chicken breast tissue slice (10 mm (x)×10 mm (y)) was sandwiched between two pieces of cover glass separated by a 2-mm spacer.

Ultrasound Beam Characterisation

The theoretical ultrasound pressure field was calculated using the fast near field method[45]. The pressure fields were first calculated at different single frequencies ranging from 1 MHz to 100 MHz and the profiles were summed with a weight accounting for transducer response and frequency spectrum of ultrasound pulse train.

The ultrasound pressure was measured in room-temperature water using a calibrated hydrophone (HGL-0085, Onda, U.S.A.). To characterise the profile of the ultrasound beam, we operated the transducer in pulse-echo mode using a pulser-receiver (5900PR, Olympus, U.S.A.) and scanned a line target (air filled polycarbonate tube, ID 22.5, OD 25, Paradigm Optics, U.S.A.) by translating the transducer in the lateral and axial direction respectively[46]. This method provides a more accurate measurement than using the hydrophone because the active diameter of the hydrophone is larger than the waist of the ultrasound beam generated by the V3330 transducer. The peak-peak voltages of the echoes were measured by an oscilloscope (DPO 3012, Tektronix, U.S.A.). Because the measurement was based on single pulse wave, side lobes were not shown.

Watershed Algorithm

The image was first binarized with a threshold that was 7 times higher than the background intensity. This step outputs a binary image in which only the pixels around the peak have the value of 1. The binary image was then segmented with a watershed algorithm and extracted the centroid of each focal spots.

Reference' contains further information on one or more embodiments of the invention.

Process Steps

FIG. 6 illustrates a method for irradiating scattering medium.

The method can comprise the following steps.

Block 600 represents modifying/modulating a particle's response to electromagnetic radiation irradiating the particle in a scattering medium (e.g., biological tissue or cells). The electromagnetic radiation is scattered by the scattering medium and modulated by the modifying into scattered electromagnetic radiation comprising a scattered field.

The modifying can comprise interacting the particle with least one (e.g., external) field selected from an electric field (e.g., generated by a voltage source), a magnetic field (e.g., generated by a magnetic coil), an electromagnetic field (e.g., generated by an electromagnetic field source such as a laser), and an acoustic field (e.g., ultrasound generated from an ultrasound transducer. Power of the field can be modulated to modulate the (e.g., nonlinear) response of the particle (e.g., triggering/modulating vibrations on the surface of the bubble to modulate the response of the bubble to the electromagnetic radiation). For example, the modifying the response of the particle/bubble can frequency shift the frequency of the electromagnetic radiation. For example, a nonlinear response can be controlled during the modifying to tailor a size of the focus. For example, the modifying can comprise controlling a pressure applied to the particle (e.g., bubble).

The particle (e.g., bubble, sphere, or other structure) can comprise a diameter in a range of 1 nanometer-50 micrometers (e.g., the particle can be nanoparticle or microparticle). The bubble can comprise a saline solution outer shell containing a gas core (e.g., a high molecular gas for increasing stability of the bubble). The bubbles or particles can be functionalized to attach to specific targets (tumors, antigens, cells).

Block 602 represents recording or measuring the scattered field (e.g., using a holographic technique, holographic storage device/medium, photorefractive crystal or film, or phase conjugate mirror). The scattered field can be recorded/measured in one or more interference patterns formed by interfering the scattered field with a reference electromagnetic field in a recording medium (e.g., camera, holographic storage device/medium, photorefractive crystal or film, or phase conjugate mirror). The scattered field can be measured using off-axis (digital or analog) holography or phase shifting holography.

Block 604 represents forming a phase conjugate field (e.g., wherein the phase conjugate field is a phase conjugate of the scattered field). The phase conjugate field can be formed using the interference patterns, wherein the phase conjugate field is a phase conjugate of the scattered field. The phase conjugate can be calculated in a computer, and generated in a DOPC device, or generated in a photorefractive crystal/film. In one or more embodiments (e.g., using a photorefractive crystal/film), the scattered field and phase conjugate field do not need to be calculated or measured—for example, the phase conjugate field can be formed/generated by reflecting/diffracting a playback reference electromagnetic beam/field from the interference pattern formed/stored in the photorefractive crystal/film.

Block 606 represents irradiating the scattering medium with the phase conjugate field, wherein the phase conjugate field forms a focus at a target defined by the particle.

Steps 600-606 can be performed within a time for scatterer shifts in the scattering medium (e.g., within 1.5 seconds)

Figure 7:
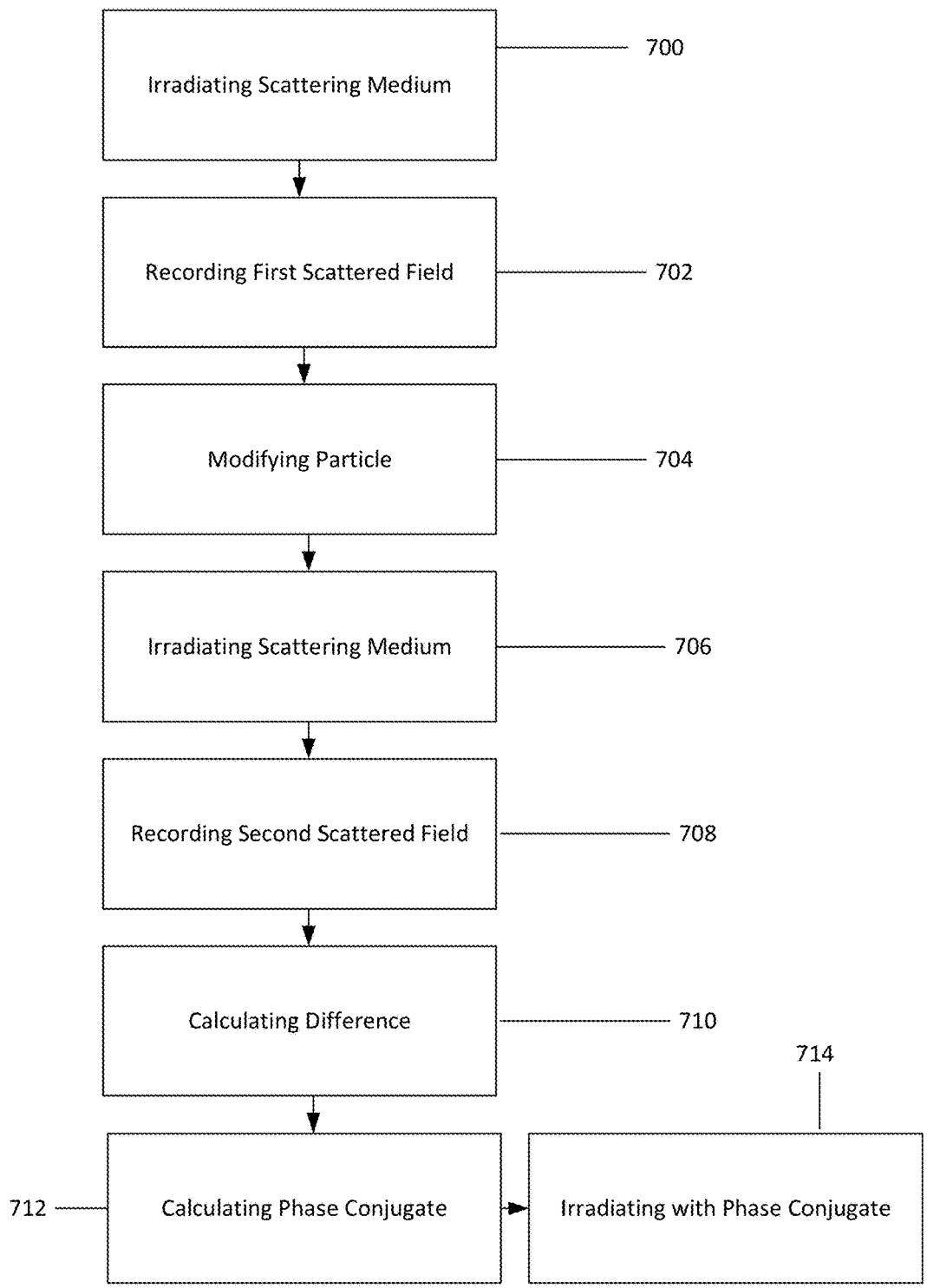
FIG. 7 illustrates a method of irradiating a scattering medium according to one or more further embodiments of the present invention.

FIG. 7 illustrates irradiating a scattering medium according to one or more further embodiments of FIG. 6.

Block 700 represents irradiating a region of the scattering medium comprising the bubble, wherein the electromagnetic radiation is scattered by the scattering medium into first scattered electromagnetic radiation comprising a first scattered field.

Block 702 represents recording the first scattered field in one or more first interference patterns.

Block 704 represents modifying (e.g., destroying or reducing/changing the size of) the bubble.

Block 706 represents irradiating the region of the scattering medium after the modifying, wherein the electromagnetic radiation is scattered by the scattering medium into second scattered electromagnetic radiation comprising a second scattered field.

Block 708 represents recording the second scattered field in one or more second interference patterns.

Block 710 represents calculating, if necessary, the scattered field comprising a difference between the first scattered field and the second scattered field.

Block 712 represents calculating/forming a phase conjugate field comprising the phase conjugate of the scattered field.

Block 714 represents irradiating the scattering medium with the phase conjugate field. In one or more embodiments of the present invention, the scattered field and the phase conjugate field are calculated in one or more processors, one or more of the processors are connected to a camera, and one or more of the processors are connected to a spatial light modulator (SLM). The interference pattern(s) can be measured on the camera, the scattered field can be calculated/measured from the interference pattern (e.g., using off-axis holography or phase shifting holography) using one or more of the processors, and the phase conjugate field can be calculated from the scattered field (i.e., by phase conjugating the scattered field, e.g., in one or more processors). The SLM can be programmed with the phase conjugate field and aligned with the camera to modulate (phase and/or amplitude of) a reference field into output electromagnetic radiation comprising the phase conjugate field. The spatial light modulator can comprise a digital micromirror device (DMD) or be based on translucent (LCD) or reflective (LCOS) liquid crystal microdisplays[48], for example.

In one or more embodiments, the scattered field (or representation of, or field associated with the scattered field) is recorded in an (e.g., interference) pattern formed in a recording medium (e.g. camera, photorefractive crystal, phase conjugate mirror). This same pattern (or a different associated pattern formed in the phase conjugate mirror such as an SLM) can comprise or generate the phase conjugate field, such that when an output beam interacts with the pattern (or different associated pattern) on the phase conjugate mirror, the output beam is formed to comprise the phase conjugate field.

For example, the interference pattern can be stored/formed in a photorefractive crystal or photorefractive film and a playback reference electromagnetic field (e.g., blank) can be reflected/diffracted/scattered off the interference pattern stored in the crystal or film to form the phase conjugate field.

The phase conjugate field can be used in many applications. For example, the focus can be used to image the scattering medium or count biological cells. The scattering medium can comprise biological cells (e.g., in biological tissue), and the focus can be formed at a depth of (e.g., at least 1 centimeter) below a surface of the scattering medium. In one or more embodiments, the focus excites a chemical composition at the target or heats the target comprising diseased cells, without damaging a surface of the biological tissue.

Figure 8:
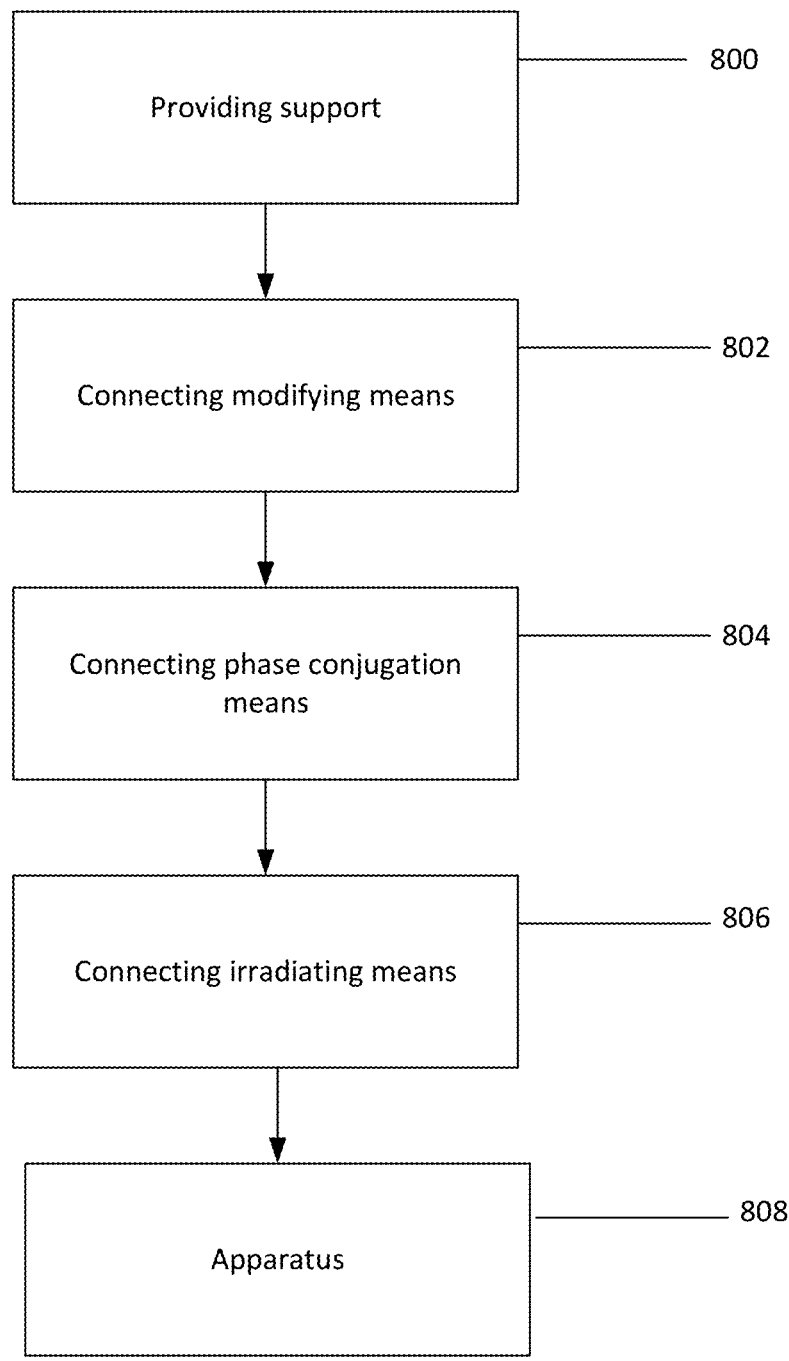
FIG. 8 illustrates a method of fabricating an apparatus for irradiating a scattering medium, according to one or more embodiments of the present invention.

FIG. 8 and FIG. 1(*a*) illustrate a method of fabricating an apparatus for irradiating a scattering medium.

Block 800 represents providing/obtaining a support (not shown, however, this can comprise, but is not limited to, an optical table, translation stage, optical mount, human body) for supporting the scattering medium/particles.

Block 802 represents connecting means (e.g., ultrasound transducer 116, field source) for (e.g., emitting a field for) modifying a particle's response to the electromagnetic radiation irradiating the particle in the scattering medium. Means can include a field source, e.g., voltage source, a magnetic field source, an electric field source, an electromagnetic field source (e.g., laser, light emitting diode) and equivalents (e.g., statutory equivalents) thereof. The means can be electromagnetically connected to the support.

Block 804 represents connecting means for recording (e.g., camera 100) the scattered field and forming (e.g., SLM, computer) a phase conjugate field (e.g., connecting phase conjugation means). In one or more embodiments, the means comprises a phase conjugate mirror such as a photorefractive crystal or film (e.g., lithium niobate or as described in one or more of the references and patent applications cross-referenced herein) or DOPC device or equivalents (e.g., statutory equivalents) thereof. The phase conjugate mirror can be electromagnetically connected to the support.

Block 806 represents connecting a laser for irradiating (e.g., with playback beam 102) the scattering medium with the phase conjugate field. A laser (same or different) can also be provided to emit the sample beam 104 (e.g., providing the electromagnetic radiation that is scattered by the scattering medium and modulated by the modifying into scattered electromagnetic radiation comprising a scattered field).

The laser can be electromagnetically connected to the support. Output electromagnetic radiation outputted from the laser interacts with the phase conjugate mirror to form the output electromagnetic radiation comprising a phase conjugate field (of the scattered field) that forms a focus at a target defined by the particle.

Block 808 represents the end result, an apparatus for irradiating a scattering medium, comprising means for modifying a particle's response to electromagnetic radiation irradiating the particle in a scattering medium, wherein the electromagnetic radiation is scattered by the scattering medium, and modulated by the modifying, into scattered electromagnetic radiation comprising a scattered field; means for recording the scattered field in an interference pattern formed by interfering the scattered field with a reference field; means for forming a phase conjugate field using the interference pattern, wherein the phase conjugate field is a phase conjugate of the scattered field; and a laser irradiating the scattering medium with the phase conjugate field, wherein the phase conjugate field forms a focus at a target defined by the particle.

In one or more embodiments, the apparatus comprises:
- an ultrasound transducer coupled to the support, wherein ultrasound emitted from the ultrasound transducer modifies a bubble's response to electromagnetic radiation irradiating the bubble in a scattering medium on the support, such that the electromagnetic radiation is scattered by the scattering medium and modulated by the modifying into scattered electromagnetic radiation comprising a scattered field;
- a digital optical phase conjugation device or photorefractive medium (crystal or film, such as lithium niobate, e.g., as described in one or more of the publications or patent applications cross-referenced herein) coupled to the support and recording the scattered field in an interference pattern formed by interfering the scattered field with a reference field; and
- a laser coupled to the digital optical phase conjugation device or the photorefractive medium, wherein the digital optical phase conjugation device or the photorefractive medium converts a reference field emitted by the laser into a phase conjugate field, and the phase conjugate field is a phase conjugate of the scattered field and forms a focus at a target defined by the bubble.

Hardware and Software Environment

Figure 9:
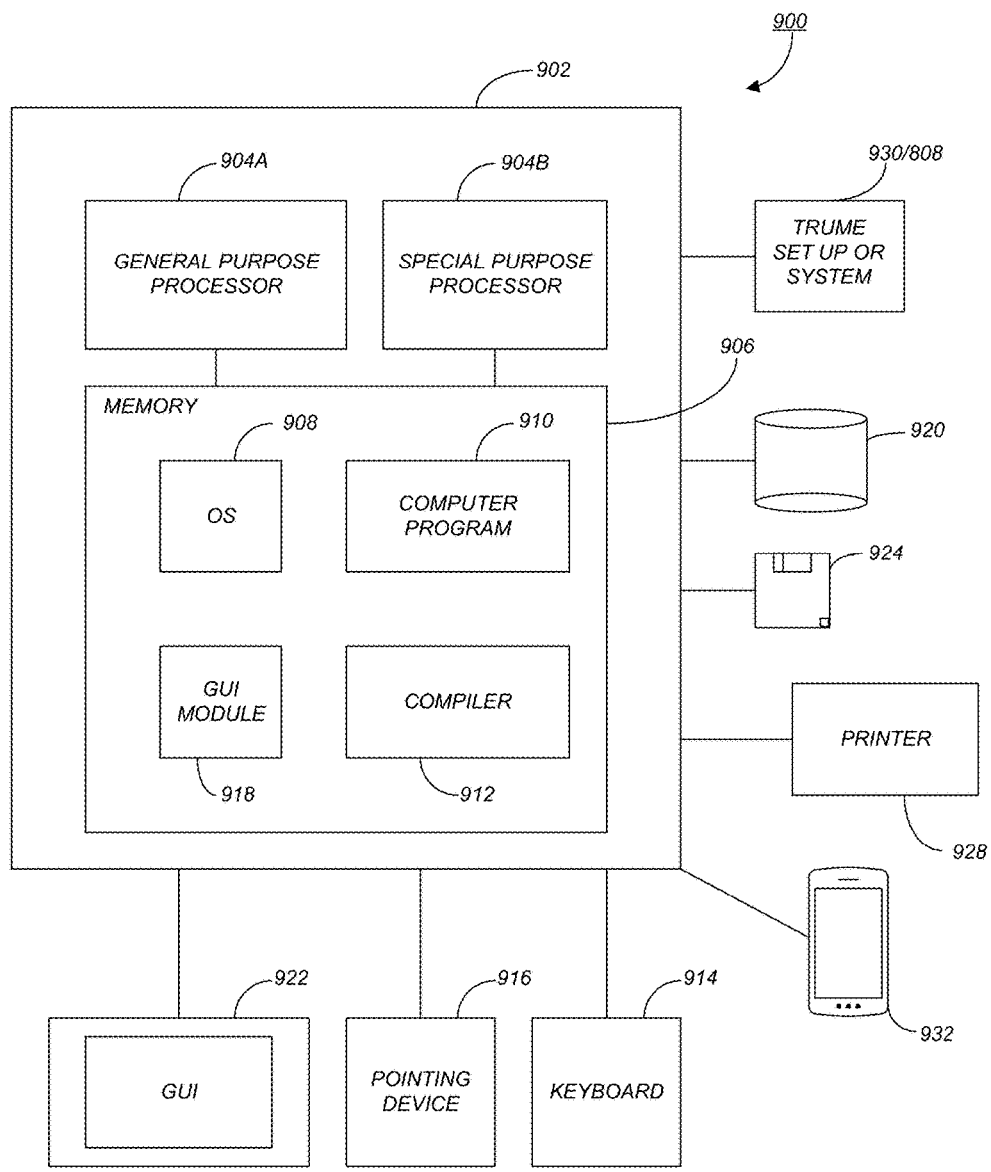
FIG. 9 is an exemplary hardware and software environment used to implement one or more embodiments of the invention.

FIG. 9 is an exemplary hardware and software environment 900 used to implement one or more embodiments of the invention. The hardware and software environment includes a computer 902 and may include peripherals. Computer 902 may be a user/client computer, server computer, or may be a database computer. The computer 902 comprises a general purpose hardware processor 904A and/or a special purpose hardware processor 904B (hereinafter alternatively collectively referred to as processor 904) and a memory 906, such as random access memory (RAM). The computer 902 may be coupled to, and/or integrated with, other devices, including input/output (I/O) devices such as a keyboard 914, a cursor control device 916 (e.g., a mouse, a pointing device, pen and tablet, touch screen, multi-touch device, etc.) and a printer 928. In one or more embodiments, computer 902 may be coupled to, or may comprise, a personal computer (e.g., desktop computer (e.g., HP Compaq™), portable or media viewing/listening device 932 (e.g., cellular/mobile device/phone, laptop, tablet, personal digital assistant, etc.) or integrated circuit, chip, or FPGA. In yet another embodiment, the computer 902 may comprise a multi-touch device, gaming system, or other internet enabled device executing on various platforms and operating systems.

In one embodiment, the computer 902 operates by the general purpose processor 904A performing instructions defined by the computer program 910 under control of an operating system 908. The computer program 910 and/or the operating system 908 may be stored in the memory 906 and may interface with the user and/or other devices to accept input and commands and, based on such input and commands and the instructions defined by the computer program 910 and operating system 908, to provide output and results.

Output/results may be presented on the display 922 (e.g., Liquid Crystal Display or Light Emitting Diode display) or provided to another device for presentation or further processing or action. The image may be provided through a graphical user interface (GUI) module 918. Although the GUI module 918 is depicted as a separate module, the instructions performing the GUI functions can be resident or distributed in the operating system 908, the computer program 910, or implemented with special purpose memory and processors.

In one or more embodiments, the display 922 is integrated with/into the computer 902 and comprises a multi-touch device having a touch sensing surface.

Some or all of the operations performed by the computer 902 according to the computer program 910 instructions may be implemented in a special purpose processor 904B. In this embodiment, the some or all of the computer program 910 instructions may be implemented via firmware instructions stored in a read only memory (ROM), a programmable read only memory (PROM) or flash memory within the special purpose processor 904B or in memory 906. The special purpose processor 904B may also be hardwired through circuit design to perform some or all of the operations to implement the present invention. Further, the special purpose processor 904B may be a hybrid processor, which includes dedicated circuitry for performing a subset of functions, and other circuits for performing more general functions such as responding to computer program 910 instructions. In one embodiment, the special purpose processor 904B is an application specific integrated circuit (ASIC).

The computer 902 may also implement a compiler 912 that allows an application or computer program 910 written in a programming language such as C, C++, Labview, Assembly, or other language to be translated into processor 904 readable code. Alternatively, the compiler 912 may be an interpreter that executes instructions/source code directly, translates source code into an intermediate representation that is executed, or that executes stored precompiled code. Such source code may be written in a variety of programming languages. After completion, the application or computer program 910 accesses and manipulates data accepted from I/O devices and stored in the memory 906 of the computer 902 using the relationships and logic that were generated using the compiler 912.

The computer 902 also optionally comprises an external communication device such as a modem, satellite link, Ethernet card, or other device for accepting input from, and providing output to, other computers 902.

In one embodiment, instructions implementing the operating system 908, the computer program 910, and the compiler 912 are tangibly embodied in a non-transitory computer-readable medium, e.g., data storage device 920, which could include one or more fixed or removable data storage devices, such as a zip drive, floppy disc drive 924, hard drive, CD-ROM drive, tape drive, etc. Further, the operating system 908 and the computer program 910 are comprised of computer program 910 instructions which, when accessed, read and executed by the computer 902, cause the computer 902 to perform the steps necessary to implement and/or use the present invention or to load the program of instructions into a memory 906, thus creating a special purpose data structure causing the computer 902 to operate as a specially programmed computer executing the method steps described herein. Computer program 910 and/or operating instructions may also be tangibly embodied in memory 906 and/or the apparatus for irradiating the scattering medium 930/808, thereby making a computer program product or article of manufacture according to the invention. As such, the terms "article of manufacture," "program storage device," and "computer program product," as used herein, are intended to encompass a computer program accessible from any computer readable device or media.

Of course, those skilled in the art will recognize that any combination of the above components, or any number of different components, peripherals, and other devices, may be used with the computer 902.

Figure 10:
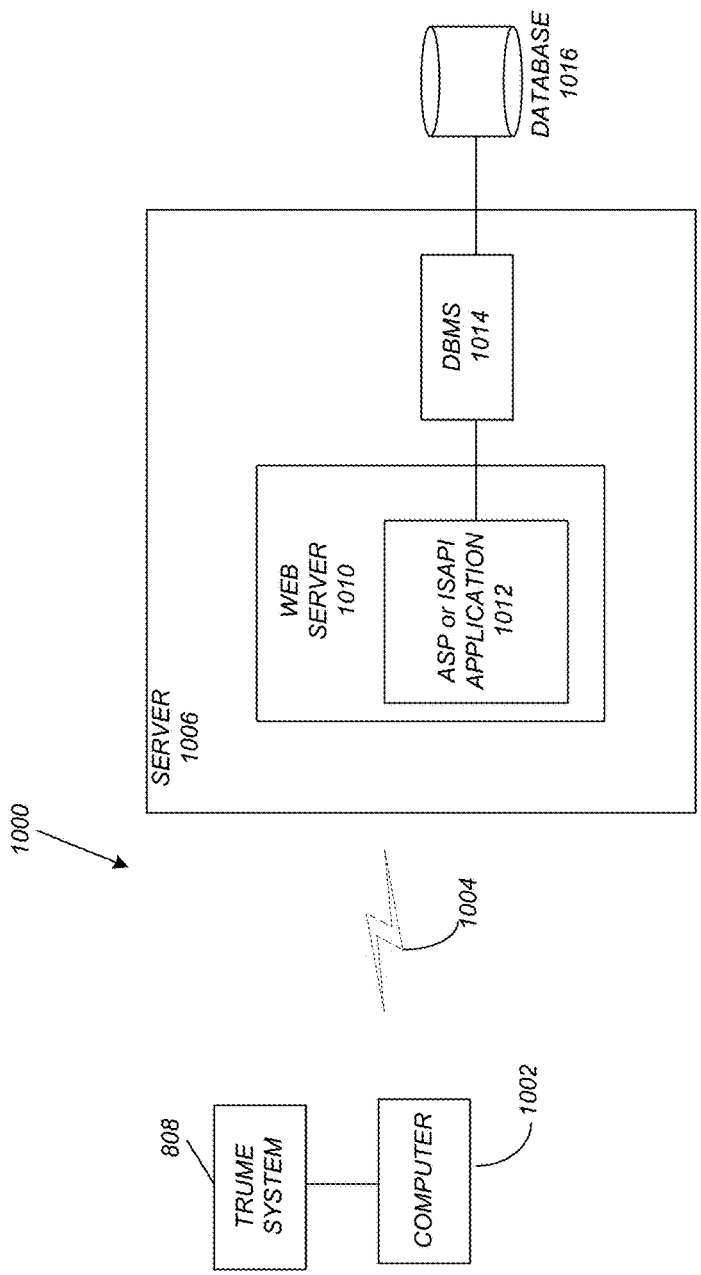
FIG. 10 schematically illustrates a typical distributed/cloud-based computer system using a network to connect client computers to server computers, according to one or more embodiments of the invention.

FIG. 10 schematically illustrates a typical distributed/cloud-based computer system 1000 using a network 1004 to connect client computers 1002 to server computers 1006. A typical combination of resources may include a network 1004 comprising the Internet, LANs (local area networks), WANs (wide area networks), SNA (systems network architecture) networks, or the like, clients 1002 that are personal computers or workstations (as set forth in FIG. 9), and servers 1006 that are personal computers, workstations, minicomputers, or mainframes (as set forth in FIG. 9). However, it may be noted that different networks such as a cellular network (e.g., GSM [global system for mobile communications] or otherwise), a satellite based network, or any other type of network may be used to connect clients 1002 and servers 1006 in accordance with embodiments of the invention.

A network 1004 such as the Internet connects clients 1002 to server computers 1006. Network 1004 may utilize ethernet, coaxial cable, wireless communications, radio frequency (RF), etc. to connect and provide the communication between clients 1002 and servers 1006.

Further, in a cloud-based computing system, resources (e.g., storage, processors, applications, memory, infrastructure, etc.) in clients 1002 and server computers 1006 may be shared by clients 1002, server computers 1006, and users across one or more networks. Resources may be shared by multiple users and can be dynamically reallocated per demand. In this regard, cloud computing may be referred to as a model for enabling access to a shared pool of configurable computing resources.

Clients 1002 may execute a client application or web browser and communicate with server computers 1006 executing web servers 1010. Such a web browser is typically a program such as MICROSOFT INTERNET EXPLORER, MOZILLA FIREFOX, OPERA, APPLE SAFARI, GOOGLE CHROME, etc. Further, the software executing on clients 1002 may be downloaded from server computer 1006 to client computers 1002 and installed. as a plug-in or ACTIVEX control of a web browser.

Web server 1010 may host an Active Server Page (ASP) or Internet Server Application Programming Interface (ISAPI) application 1012, which may be executing scripts. The scripts invoke objects that execute business logic (referred to as business objects). The business objects then manipulate data in database 1016 through a database management system (DBMS) 1014. Alternatively, database 1016 may be part of, or connected directly to, client 1002 instead of communicating/obtaining the information from database 1016 across network 1004. Further, server 1006 may utilize MICROSOFT'S TRANSACTION SERVER (MTS) to access required data stored in database 1016 via an interface such as ADO (Active Data Objects), OLE DB (Object Linking and Embedding DataBase), or ODBC (Open DataBase Connectivity).

Generally, these components 1000-1016 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Although the terms "user computer", "client computer", and/or "server computer" are referred to herein, it is understood that such computers 1002 and 1006 may be interchangeable and may further include thin client devices with limited or full processing capabilities, portable devices such as cell phones, notebook computers, pocket computers, multi-touch devices, and/or any other devices with suitable processing, communication, and input/output capability.

Of course, those skilled in the art will recognize that any combination of the above components, or any number of different components, peripherals, and other devices, may be used with computers 1002 and 1006.

Embodiments of the invention are implemented as a software application on a client 1002 or server computer 1006. Further, as described above, the client 1002 or server computer 1006 may comprise a thin client device or a portable device that has a multi-touch-based display.

The hardware and software environment can be used to control various aspects of the invention (e.g., signal flow), and perform algorithms or calculations as disclosed herein.

Figure 11:
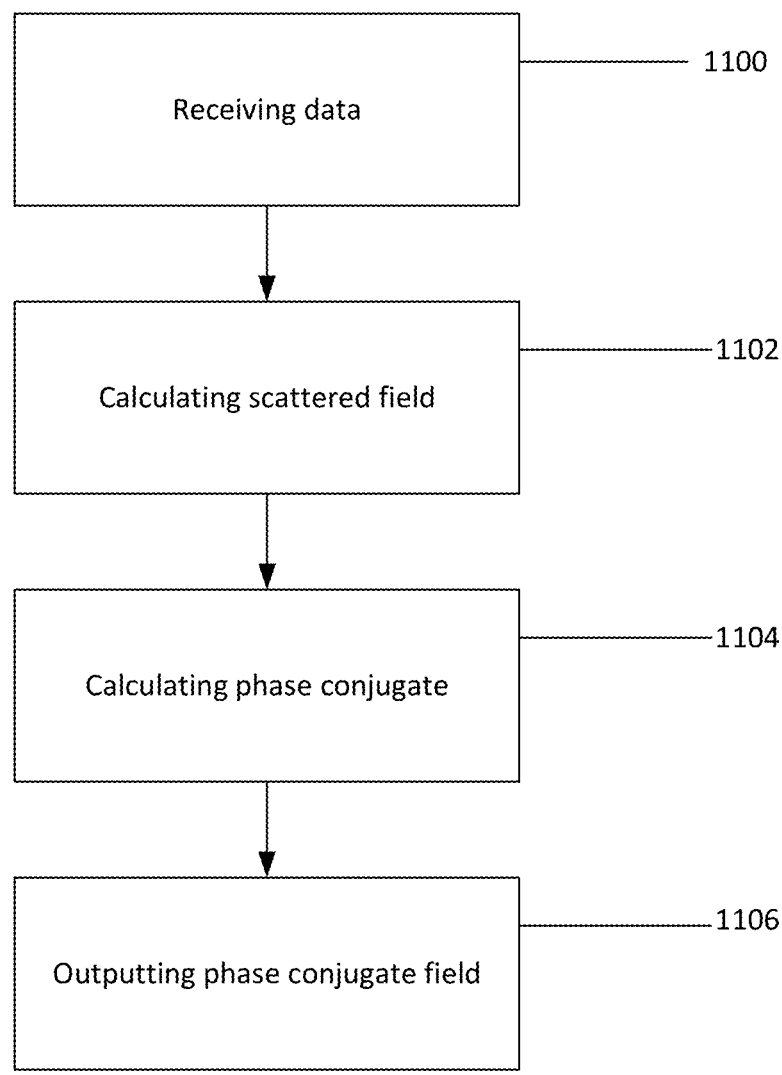
FIG. 11 illustrates a method of irradiating a scattering medium, according to one or more embodiments of the invention.

FIG. 11 illustrates a method of irradiating a scattering medium.

Block 1100 represents receiving, in computer 900, data from which the scattering medium can be obtained/computed (e.g., receiving an interference pattern formed by interfering a scattered field with a reference field, the scattered field obtained from a process comprising modifying a particle's response to electromagnetic radiation irradiating the particle in a scattering medium, wherein the electromagnetic radiation is scattered by the scattering medium and modulated by the modifying into scattered electromagnetic radiation comprising the scattered field).

Block 1102 represents calculating, in computer 900, the scattered field. For example, the scattered field can be calculated by computing a difference between the first scattered field and the second scattered field, the first and second scattered fields.

Block 1104 represents calculating/computing, in computer 900, a phase conjugate of the scattered field to form a phase conjugate field.

Block 1106 represents outputting, from computer 900, the phase conjugate field to a phase conjugate mirror, wherein the phase conjugate mirror irradiates the scattering medium with the phase conjugate field and the phase conjugate field forms a focus at a target defined by the particle.

REFERENCES

The following references are incorporated by reference herein.

1. Mosk, A. P., Lagendijk, A., Lerosey, G. & Fink, M. Controlling waves in space and time for imaging and focusing in complex media. Nature Photonics 6, 283-292 (2012).
2. Vellekoop, I. M. Feedback-based wavefront shaping. Opt. Express 23, 12189 (2015).
3. Kim, M., Choi, W., Choi, Y., Yoon, C. & Choi, W. Transmission matrix of a scattering medium and its applications in biophotonics. Opt. Express 23, 12648 (2015).
4. Yu, H. et al. Recent advances in wavefront shaping techniques for biomedical applications. Curr. Appl. Phys. 15, 632-641 (2015).
5. Vellekoop, I. M. & Mosk, A. P. Focusing coherent light through opaque strongly scattering media. Opt. Lett. 32, 2309-2311 (2007).
6. Yaqoob, Z., Psaltis, D., Feld, M. S. & Yang, C. Optical phase conjugation for turbidity suppression in biological samples. Nat Phot. 2, 110-115 (2008).
7. Cui, M. & Yang, C. Implementation of a digital optical phase conjugation system and its application to study the robustness of turbidity suppression by phase conjugation. Opt. Express 18, 3444-3455 (2010).
8. Popoff, S. M. et al. Measuring the Transmission Matrix in Optics: An Approach to the Study and Control of Light Propagation in Disordered Media. Phys. Rev. Lett. 104, 100601 (2010).
9. Yu, H. et al. Measuring Large Optical Transmission Matrices of Disordered Media. Phys. Rev. Lett. 111, 153902 (2013).
10. Chaigne, T. et al. Controlling light in scattering media non-invasively using the photoacoustic transmission matrix. Nat. Photonics 8, 58-64 (2013).
11. Hsieh, C., Pu, Y., Grange, R. & Psaltis, D. Digital phase conjugation of second harmonic radiation emitted by nanoparticles in turbid media. Opt. Express 18, 533-537 (2010).
12. Vellekoop, I. M., Cui, M. & Yang, C. Digital optical phase conjugation of fluorescence in turbid tissue. Appl. Phys. Lett. 101, 81108 (2012).
13. Katz, O., Small, E., Guan, Y. & Silberberg, Y. Non-invasive nonlinear focusing and imaging through strongly scattering turbid layers. Optica 1, 170 (2014).
14. Zhou, E. H., Ruan, H., Yang, C. & Judkewitz, B. Focusing on moving targets through scattering samples. Optica 1, 227 (2014).
15. Ma, C., Xu, X., Liu, Y. & Wang, L. V. Time-reversed adapted-perturbation (TRAP) optical focusing onto dynamic objects inside scattering media. Nat. Photonics 8, 931-936 (2014).
16. Kong, F. et al. Photoacoustic-guided convergence of light through optically diffusive media. Opt. Lett. 36, 2053-5 (2011).
17. Caravaca-Aguirre, A. M. et al. High contrast three-dimensional photoacoustic imaging through scattering media by localized optical fluence enhancement. Opt. Express 21, 26671 (2013).
18. Lai, P., Wang, L., Tay, J. W. & Wang, L. V. Photoacoustically guided wavefront shaping for enhanced optical focusing in scattering media. Nat. Photonics 9, 126-132 (2015).
19. Xu, X., Liu, H. & Wang, L. V. Time-reversed ultrasonically encoded optical focusing into scattering media. Nat. Photonics 5, 154-157 (2011).
20. Wang, Y. M., Judkewitz, B., DiMarzio, C. A. & Yang, C. Deep-tissue focal fluorescence imaging with digitally time-reversed ultrasound-encoded light. Nat Commun 3, 928 (2012).
21. Si, K., Fiolka, R. & Cui, M. Fluorescence imaging beyond the ballistic regime by ultrasound pulse guided digital phase conjugation. Nat. Photonics 6, 657-661 (2012).
22. Jong, M., Ruan, H., Judkewitz, B. & Yang, C. Model for estimating the penetration depth limit of the time-reversed ultrasonically encoded optical focusing technique. Opt Express 22, 5787-5807 (2014).
23. Kothapalli, S.-R. & Wang, L. V. Ultrasound-modulated optical microscopy. J. Biomed. Opt. 13, 054046
24. Si, K., Fiolka, R. & Cui, M. Breaking the spatial resolution barrier via iterative sound-light interaction in deep tissue microscopy. Sci. Rep. 2, 748 (2012).
25. Ruan, H., Jang, M., Judkewitz, B. & Yang, C. Iterative time-reversed ultrasonically encoded light focusing in backscattering mode. Sci. Rep. 4, 7156 (2014).
26. Suzuki, Y., Tay, J. W., Yang, Q. & Wang, L. V. Continuous scanning of a time-reversed ultrasonically encoded optical focus by reflection-mode digital phase conjugation. Opt. Lett. 39, 3441-4 (2014).
27. Judkewitz, B., Wang, Y. & Horstmeyer, R. Speckle-scale focusing in the diffusive regime with time reversal of variance-encoded light (TROVE). Nat. Photonics 7, 300-305 (2013).
28. Lindner, J. R. Microbubbles in medical imaging: current applications and future directions. 3, 527-532 (2004).
29. Goertz, D. E. et al. High frequency nonlinear B-scan imaging of microbubble contrast agents. IEEE Trans. Ultrason. Ferroelectr. Freq. Control 52, 65-79 (2005).
30. Benchimol, M. J. et al. Phospholipid/Carbocyanine Dye-Shelled Microbubbles as Ultrasound-Modulated Fluorescent Contrast Agents. Soft Matter 9, 2384-2388 (2013).
31. Liu, Y., Feshitan, J. A., Wei, M.-Y., Borden, M. A. & Yuan, B. Ultrasound-modulated fluorescence based on fluorescent microbubbles. J. Biomed. Opt. 19, 085005 (2014).
32. Ruan, H., Mather, M. L. & Morgan, S. P. Ultrasound modulated optical tomography contrast enhancement with non-linear oscillation of microbubbles. Quant. Imaging Med. Surg. 5, 9-16 (2015).
33. Jang, M., Ruan, H., Zhou, H., Judkewitz, B. & Yang, C. Method for auto-alignment of digital optical phase conjugation systems based on digital propagation. Opt. Express 22, 14054-71 (2014).
34. Yamaguchi, I., Matsumura, T. & Kato, J.-I. Phase-shifting color digital holography. Opt. Lett. 27, 1108-10 (2002).
35. Vellekoop, I. M. Controlling the propagation of light in disordered scattering media. PhD Thesis, Univ. Twente (2008).
36. Shekhar, H., Rychak, J. J. & Doyley, M. M. Modifying the size distribution of microbubble contrast agents for high-frequency subharmonic imaging. Med. Phys. 40, 082903 (2013).
37. Pancholi, K. P., Farook, U., Moaleji, R., Stride, E. & Edirisinghe, M. J. Novel methods for preparing phospholipid coated microbubbles. Eur. Biophys. J. 37, 515-20 (2008).
38. Palanchon, P., Klein, J. & de Jong, N. Production of standardized air bubbles: Application to embolism studies. Rev. Sci. Instrum. 74, 2558 (2003).
39. Jong, M. et al. Relation between speckle decorrelation and optical phase conjugation (OPC)-based turbidity suppression through dynamic scattering media: a study on in vivo mouse skin. Biomed. Opt. Express 6, 72 (2015).

40. Chomas, J. E., Dayton, P., Allen, J., Morgan, K. & Ferrara, K. W. Mechanisms of contrast agent destruction. IEEE Trans. Ultrason. Ferroelectr. Freq. Control 48, 232-48 (2001).

41. Ferrara, K., Pollard, R. & Borden, M. Ultrasound microbubble contrast agents: fundamentals and application to gene and drug delivery. Annu. Rev. Biomed. Eng. 9, 415-47 (2007).

42. Shapiro, M. G. et al. Biogenic gas nanostructures as ultrasonic molecular reporters. Nat. Nanotechnol. 9, 311-6 (2014).

43. El-Sayed, I. H., Huang, X. & El-Sayed, M. A. Selective laser photo-thermal therapy of epithelial carcinoma using anti-EGFR antibody conjugated gold nanoparticles. Cancer Lett. 239, 129-35 (2006).

44. Gradinaru, V., Mogri, M., Thompson, K. R., Henderson, J. M. & Deisseroth, K. Optical deconstruction of parkinsonian neural circuitry. Science 324, 354-9 (2009).

45. Chen, D. & McGough, R. J. A 2D fast near-field method for calculating near-field pressures generated by apodized rectangular pistons. J. Acoust. Soc. Am. 124, 1526-37 (2008).

46. Raum, K. & O'Brien, W. D. Pulse-echo field distribution measurement technique for high-frequency ultrasound sources. IEEE Trans. Ultrason. Ferroelectr. Freq. Control 44, 810-815 (1997).

47. Haowen Ruan et. al., "Optical focusing inside scattering media with time-reversed ultrasound microbubble encoded light," Haowen Ruan, Mooseok Jang, and Changhuei Yang, Nature communications, 6:8968|DOI: 10.1038/ncomms9968|www.nature.com/naturecommunications (Nov. 24, 2015) and Supplementary Information.

48. website entitled/accessible from "http://holoeye.com/spatial-light-modulators/."

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method for irradiating scattering medium, comprising:
    modifying a particle's response to electromagnetic radiation irradiating the particle in a scattering medium, wherein the electromagnetic radiation is scattered by the scattering medium, and modulated by the modifying, into scattered electromagnetic radiation comprising a scattered field;
    forming a phase conjugate field, wherein the phase conjugate field is a phase conjugate of the scattered field; and
    irradiating the scattering medium with the phase conjugate field, wherein the phase conjugate field forms a focus at a target defined by the particle; and wherein:
    the scattered field and the phase conjugate field are calculated in one or more processors, one or more of the processors are connected to a camera and one or more of the processors are connected to a spatial light modulator;
    the scattered field is interfered with a reference field to form one or more interference patterns measured on the camera;
    the scattered field is measured from the interference patterns using the one or more processors; and
    the SLM is programmed with the phase conjugate field, aligned with the camera, and forms output electromagnetic radiation comprising the phase conjugate field.

2. The method of claim 1, wherein the modifying comprises interacting the particle with least one field selected from an electric field, a magnetic field, an electromagnetic field, and an acoustic field.

3. The method of claim 2, wherein the particle comprises a bubble.

4. The method of claim 3, further comprising:
    irradiating a region of the scattering medium comprising the bubble, wherein the electromagnetic radiation is scattered by the scattering medium into first scattered electromagnetic radiation comprising a first scattered field;
    recording the first scattered field in one or more first interference patterns;
    the modifying of the bubble;
    irradiating the region of the scattering medium after the modifying, wherein the electromagnetic radiation is scattered by the scattering medium into second scattered electromagnetic radiation comprising a second scattered field;
    recording the second scattered field in one or more second interference patterns; and
    calculating the scattered field comprising a difference between the first scattered field and the second scattered field.

5. The method of claim 4, wherein the modifying comprises destroying the bubble.

6. The method of claim 3, wherein the modifying field comprises ultrasound.

7. The method of claim 1, wherein the response is a nonlinear response controlled during the modifying to tailor a size of the focus.

8. The method of claim 1, wherein the modifying comprises controlling a pressure applied to the particle comprising a bubble.

9. The method of claim 1, wherein the scattered field is measured using off-axis holography or phase shifting holography.

10. The method of claim 1, further comprising:
    recording the scattered field in an interference pattern in formed in a photorefractive crystal or photorefractive film;
    reflecting or diffracting a reference electromagnetic field off the interference pattern formed in the photorefractive crystal or film to form the phase conjugate field.

11. The method of claim 1, wherein:
    the focus is used to image the scattering medium,
    the scattering medium comprises biological cells, and
    the focus is formed at a depth of at least 1 cm below a surface of the scattering medium.

12. The method of claim 1, wherein:
    the scattering medium comprises biological tissue,
    the focus excites a chemical composition at the target or heats the target comprising diseased cells, without damaging a surface of the biological tissue.

13. The method of claim 1, wherein the focus is used to count biological cells in the scattering medium.

14. An apparatus for irradiating a scattering medium, comprising:
a support;
a field source electromagnetically connected to the support, wherein:
a field emitted from the field source modifies a particle's response to electromagnetic radiation irradiating the particle in a scattering medium on the support, and
the electromagnetic radiation is scattered by the scattering medium and modulated by the modifying into scattered electromagnetic radiation comprising a scattered field;
a phase conjugate mirror electromagnetically connected to the support;
a laser electromagnetically connected to the phase conjugate mirror, wherein:
output electromagnetic radiation outputted from the laser interacts with the phase conjugate mirror to form the output electromagnetic radiation comprising a phase conjugate field that forms a focus at a target defined by the particle, and the phase conjugate field comprises a phase conjugate of the scattered field.

15. The apparatus of claim 14, wherein the field source comprises an ultrasound transducer and the particle comprises a bubble.

16. The apparatus of claim 14, wherein the phase conjugate mirror comprises a photorefractive crystal or photorefractive film, the photorefractive crystal or photorefractive film recording the scattered field in an interference pattern formed in the photorefractive crystal or photorefractive film.

17. The apparatus of claim 14, further comprising:
a camera capable of measuring an interference pattern between a reference field and the scattered field;
one or more processors connected to the camera, the one or more processors capable of calculating the scattered field from the interference pattern;
the phase conjugate mirror comprising a spatial light modulator (SLM) aligned with the camera; and
one or more processors connected to the spatial light modulator (SLM), the one or more processors connected to the spatial light modulator capable of calculating the phase conjugate field from the scattered field; and wherein:
the SLM programmed with the phase conjugate field forms the output electromagnetic radiation.

\* \* \* \* \*